(12) United States Patent
Katsikis et al.

(10) Patent No.: US 9,006,194 B2
(45) Date of Patent: Apr. 14, 2015

(54) COMPOSITIONS AND METHODS FOR DIMINISHING VIRAL INFECTION AND INFLAMMATION ASSOCIATED WITH VIRAL INFECTION

(75) Inventors: Peter D. Katsikis, Merion Station, PA (US); Alina C. Boesteanu, Willow Grove, PA (US); Sefik S. Alkan, Basel (CH)

(73) Assignee: Drexel University, Philadelphia, PA (US)

( * ) Notice: Subject to any disclaimer, the term of this patent is extended or adjusted under 35 U.S.C. 154(b) by 163 days.

(21) Appl. No.: 13/140,521

(22) PCT Filed: Dec. 17, 2009

(86) PCT No.: PCT/US2009/068510
§ 371 (c)(1),
(2), (4) Date: Sep. 7, 2011

(87) PCT Pub. No.: WO2010/080509
PCT Pub. Date: Jul. 15, 2010

(65) Prior Publication Data
US 2011/0313022 A1    Dec. 22, 2011

Related U.S. Application Data

(60) Provisional application No. 61/139,275, filed on Dec. 19, 2008.

(51) Int. Cl.
*A61K 31/713* (2006.01)
*A61K 31/7105* (2006.01)
*A61K 31/711* (2006.01)
*A61K 31/7125* (2006.01)
*C12N 15/117* (2010.01)

(52) U.S. Cl.
CPC .......... *A61K 31/713* (2013.01); *A61K 31/7105* (2013.01); *A61K 31/711* (2013.01); *A61K 31/7125* (2013.01); *C12N 15/117* (2013.01); *C12N 2310/17* (2013.01); *C12N 2310/315* (2013.01); *C12N 2310/332* (2013.01); *G01N 2500/10* (2013.01)

(58) Field of Classification Search
None
See application file for complete search history.

(56) References Cited

U.S. PATENT DOCUMENTS

| 5,176,996 | A | | 1/1993 | Hogan et al. |
| 5,945,522 | A | * | 8/1999 | Cohen et al. ................. 536/23.1 |
| 2006/0121460 | A1 | | 6/2006 | Medzhitov |

OTHER PUBLICATIONS

Haas, et al. (Mar. 14, 2008) The DNA Sugar Backbone 2' Deoxyribose Determines Toll-like Receptor 9 Activation. Immunity, v.28(3):315-23.*
Robbins, et al., "2'-O-methyl-modified RNAs Act as TLR7 Antagonists," *Molecular Therapy*, Sep. 2007, 15(9):1663-1669.
Wagner, "The sweetness of the DNA backbone drives Toll-like receptor 9," *Current Opinion in Immunology*, 2008, 20:396-400.
Meier, et al., "MyD88-Dependent Immune Activation Mediated by Human Immunodeficiency Virus Type 1-Encoded Toll-Like Receptor Ligands," *Journal of Virology*, Aug. 2007, 81(15):8180-8191.
International Search Report for PCT/US09/68510, dated May 27, 2010.
International Preliminary Report on Patentability for PCT/US09/68510, dated Jun. 21, 2011.

* cited by examiner

*Primary Examiner* — Jennifer McDonald
(74) *Attorney, Agent, or Firm* — Saul Ewing LLP; Kathryn Doyle

(57) ABSTRACT

The invention relates to compositions and methods for preventing and diminishing virus infection. The invention further relates to compositions and methods for diminishing inflammation associated with viral infection. The invention also relates to compositions and methods for interfering with TLR activation, and thereby diminishing inflammation associated with viral infection.

6 Claims, 12 Drawing Sheets

COMPOSITIONS AND METHODS FOR DIMINISHING VIRAL INFECTION AND INFLAMMATION ASSOCIATED WITH VIRAL INFECTION

CROSS-REFERENCE TO RELATED APPLICATION

The present application is a 35 U.S.C. §371 national phase application from, and claiming priority to, International Application PCT/US2009/068510, filed Dec. 17, 2009, and published under PCT Article 21(2) in English, which is entitled to priority under 35 U.S.C. §119(e) to U.S. Provisional Application No. 61/139,275, filed Dec. 19, 2008, which applications are incorporated by reference herein in their entireties.

STATEMENT REGARDING FEDERALLY SPONSORED RESEARCH OR DEVELOPMENT

This invention was made with government support under Contract No. R01AI046719 awarded by the National Institutes of Health (NIH). The government has certain rights in the invention.

BACKGROUND

Inflammation associated with viral infections, such as influenza virus infection, is the cause of much morbidity and mortality. The severity of both seasonal and pandemic influenza virus infection has been associated with inflammation and the over-production of proinflammatory cytokines.

Inflammation is the complex biological response to stimuli including pathogens, such as viruses (Serhan and Ward, 1998, Molecular and Cellular Basis of Inflammation, Humana Press, Clifton, N.J.). Examples of plasma-derived mediators of inflammation include, among others, bradykinin, C3, C5a, Factor XII, Membrane attack complex (i.e., C5b, C6, C7, C8, C9), plasmin, and thrombin. Examples of cell-derived mediators of inflammation include, among others, histamine, IFN-γ, IL-1, IL-8, TNFα, leukotrienes, nitric oxide, and prostaglandins.

Toll-like receptors (TLRs) are a class of receptors that activate immune responses after recognizing molecules derived from pathogens. TLRs are pattern recognition receptors (PRR) that can recognize molecules broadly shared by pathogens. A number of TLRs (e.g., TLR7, TLR8, TLR9), along with other molecules (RIG-1, MDA), are known to recognize RNA from viruses, such as influenza virus and HIV (Meier et al., 2007, J. Virology 81:8180-8191). The activation of TLR leads to inflammation.

In addition to controlling inflammation occurring after infection, agents and methods are under development to prevent infection from occurring in the first place. One strategy for preventing infection, for example by preventing the transmission of infectious agents (e.g., HIV) during vaginal sex, is the deployment of topical, female-applied, microbicidal agent that can be applied directly to the genital tract to diminish the probability of acquiring or transmitting HIV. Candidate microbicides presently under development for intravaginal application include alkyl sulfate surfactants, chemokine co-receptor analogues and other compounds that specifically or non-specifically block virus-host cell interactions. Such microbicides may also be useful to block rectal transmission of viruses. An ideal microbicide would fulfill a number of criteria including having in vivo activity against both cell-free and cell-associated HIV, would also not adversely affect the protective integrity of vaginal and cervical mucosal epithelium.

The ability to interfere with the activation of TLRs, such as TLR7, TLR8 and TLR9, to diminish the severity of inflammation associated with viral infection will aid in diminishing the morbidity and mortality contributed by inflammation associated with viral infection. Moreover, the ability to interfere with the transmission of infectious agents, such as viruses, will also aid in diminishing the morbidity and mortality contributed by infection. To date, there are no compounds that effectively provide such interference. The present invention fulfills these needs.

SUMMARY OF THE INVENTION

In one embodiment, the invention is a nucleic acid composition having a nucleic acid sequence that is homologous to all or a fragment of a nucleic acid reference sequence of the group consisting of SEQ ID NO:1, SEQ ID NO:2, SEQ ID NO:3, SEQ ID NO:4 and SEQ ID NO:5. The nucleic acid compositions can be a DNA, an RNA, a baseless backbone, a nearly baseless backbone or a baseless phosphorothioate backbone. The nucleic acid compositions can single-stranded or double-stranded. In various embodiments, the nucleic acid can be from about 5 to about 10 nucleotides long, from about 10 to about 15 nucleotides long, from about 15 to about 20 nucleotides long, from about 20 to about 25 nucleotides long, or from about 25 to about 30 nucleotides long. In some embodiments, the nucleic acid compositions of the invention can be formulated with at least one pharmaceutically acceptable carrier, or at least one pharmaceutically acceptable diluent, or at least one pharmaceutically acceptable solubilizing agent, or combinations thereof. The nucleic acid compositions of the invention are useful for diminishing inflammation associated with viral infection. Further, the nucleic acid compositions of the invention are useful for diminishing inflammation associated with viral infection by binding to TLR (e.g. TLR7, TLR8, and TLR9) and inhibiting TLR activation. Moreover, the nucleic acid compositions of the invention are useful for preventing infection. Further, the nucleic acid compositions of the invention are useful for interfering with the transmission of a virus to a cell.

In another embodiment, the invention is a method of identifying a nucleic acid inhibitor of TLR activation that includes the steps of: 1) measuring the level of a marker of inflammation at a first timepoint in a biological sample derived from a virus-infected individual; 2) contacting the virus-infected individual with a nucleic acid; 3) measuring the level of the marker of inflammation at a second timepoint in a biological sample derived from the virus-infected individual; and when the level of the marker of inflammation measured at the second timepoint is diminished as compared with the level of the marker of inflammation measured at the first timepoint, the nucleic acid is identified as an inhibitor of TLR activation. In various embodiments, the nucleic acid inhibitor identified is homologous to all or a fragment of at least one of the group nucleic acid reference sequences consisting of SEQ ID NO:1, SEQ ID NO:2, SEQ ID NO:3, SEQ ID NO:4 and SEQ ID NO:5. The nucleic acid inhibitor can be a DNA, an RNA, a baseless backbone, a nearly baseless backbone or a baseless phosphorothioate backbone. The nucleic acid inhibitor can single-stranded or double-stranded. In various embodiments, the nucleic acid inhibitor can be from about 5 to about 10 nucleotides long, from about 10 to about 15 nucleotides long, from about 15 to about 20 nucleotides long, from about 20 to about 25 nucleotides long, or from about 25 to about 30 nucleotides long. In various embodiments, the TLR inhibited by the nucleic acid inhibitor of the invention can be TLR7, TLR8, TLR9, or combinations thereof. In various embodiments, the marker of inflammation assessed can be a cytokine, an immune cell, or combinations thereof.

In a further embodiment, the invention is a method of inhibiting TLR activation including contacting a virus-infected individual with a nucleic acid inhibitor of TLR activation. In various embodiments, the sequence of the nucleic acid inhibitor is homologous to all or a fragment of a nucleic acid reference sequence of the group consisting of SEQ ID NO:1, SEQ ID NO:2, SEQ ID NO:3, SEQ ID NO:4 and SEQ ID NO:5. The nucleic acid inhibitor can be at least one of a DNA, an RNA, a baseless backbone, a nearly baseless backbone or a baseless phosphorothioate backbone. The nucleic acid inhibitor can single-stranded or double-stranded. In various embodiments, the nucleic acid inhibitor can be from about 5 to about 10 nucleotides long, from about 10 to about 15 nucleotides long, from about 15 to about 20 nucleotides long, from about 20 to about 25 nucleotides long, or from about 25 to about 30 nucleotides long. In some embodiments, the TLR inhibited by the nucleic acid inhibitor of the invention can be TLR7, TLR8, TLR9, or combinations thereof.

In one embodiment, the invention is a method of diminishing the level of inflammation in a virus-infected individual including contacting a virus-infected individual with a nucleic acid inhibitor of TLR activation, wherein the virus-infected individual's level of inflammation is diminished. In various embodiments, the sequence of the nucleic acid inhibitor is homologous to all or a fragment of a nucleic acid reference sequence of the group consisting of SEQ ID NO:1, SEQ ID NO:2, SEQ ID NO:3, SEQ ID NO:4 and SEQ ID NO:5. The nucleic acid inhibitor can be at least one of a DNA, an RNA, a baseless backbone, a nearly baseless backbone or a baseless phosphorothioate backbone. The nucleic acid inhibitor can single-stranded or double-stranded. In various embodiments, the nucleic acid inhibitor can be from about 5 to about 10 nucleotides long, from about 10 to about 15 nucleotides long, from about 15 to about 20 nucleotides long, from about 20 to about 25 nucleotides long, or from about 25 to about 30 nucleotides long. In some embodiments, the TLR inhibited by the nucleic acid inhibitor of the invention can be TLR7, TLR8, TLR9, or combinations thereof. In various embodiments, the level of inflammation before and after practicing the steps of the method is assessed by measuring the level of at least one marker of inflammation, including a cytokine or an immune cell.

In another embodiment, the invention is a method of identifying a nucleic acid inhibitor of viral infection including the steps of: 1) contacting a virus with a nucleic acid; 2) contacting a first cell population with the virus; 3) measuring the level of a marker of virus infection in a biological sample derived from the first cell population; 4) measuring the level of the marker of virus infection in a biological sample derived from a second cell population that was contacted with a virus not contacted with the nucleic acid; wherein when the level of the marker of infection measured in the biological sample derived from the first cell population is diminished as compared with the level of the marker of infection measured in the biological sample derived from the second cell population, the nucleic acid is identified as an inhibitor of virus infection. In various embodiments, the nucleic acid inhibitor identified is homologous to all or a fragment of at least one of the group nucleic acid reference sequences consisting of SEQ ID NO:1, SEQ ID NO:2, SEQ ID NO:3, SEQ ID NO:4 and SEQ ID NO:5. The nucleic acid inhibitor can be at least one of a DNA, an RNA, a baseless backbone, a nearly baseless backbone or a baseless phosphorothioate backbone. The nucleic acid inhibitor can single-stranded or double-stranded. In various embodiments, the nucleic acid inhibitor can be from about 5 to about 10 nucleotides long, from about 10 to about 15 nucleotides long, from about 15 to about 20 nucleotides long, from about 20 to about 25 nucleotides long, or from about 25 to about 30 nucleotides long. In some embodiments, the marker of infection assessed can be a virus structural protein, a virus nonstructural protein, a virus nucleic acid sequence, or combinations thereof.

In a further embodiment, the invention is a method of inhibiting virus infection including contacting a virus with a nucleic acid inhibitor of virus infection; wherein the sequence of the nucleic acid inhibitor is homologous to all or a fragment of a nucleic acid reference sequence. In various embodiments, the nucleic acid inhibitor is homologous to all or a fragment of at least one of the group nucleic acid reference sequences consisting of SEQ ID NO:1, SEQ ID NO:2, SEQ ID NO:3, SEQ ID NO:4 and SEQ ID NO:5. The nucleic acid inhibitor can be at least one of a DNA, an RNA, a baseless backbone, a nearly baseless backbone or a baseless phosphorothioate backbone. The nucleic acid inhibitor can single-stranded or double-stranded. In various embodiments, the nucleic acid inhibitor can be from about 5 to about 10 nucleotides long, from about 10 to about 15 nucleotides long, from about 15 to about 20 nucleotides long, from about 20 to about 25 nucleotides long, or from about 25 to about 30 nucleotides long. In some embodiments, the marker of infection assessed can be a virus structural protein, a virus nonstructural protein, a virus nucleic acid sequence, or combinations thereof.

In a still further embodiment, the invention is a method of diminishing the level of transmission of a virus to a cell comprising contacting the virus with a nucleic acid inhibitor and contacting a cell with the virus; wherein the level of transmission of the virus to the cell is diminished. In various embodiments, the nucleic acid inhibitor is homologous to all or a fragment of at least one of the group nucleic acid reference sequences consisting of SEQ ID NO:1, SEQ ID NO:2, SEQ ID NO:3, SEQ ID NO:4 and SEQ ID NO:5. The nucleic acid inhibitor can be at least one of a DNA, an RNA, a baseless backbone, a nearly baseless backbone or a baseless phosphorothioate backbone. The nucleic acid inhibitor can single-stranded or double-stranded. In various embodiments, the nucleic acid inhibitor can be from about 5 to about 10 nucleotides long, from about 10 to about 15 nucleotides long, from about 15 to about 20 nucleotides long, from about 20 to about 25 nucleotides long, or from about 25 to about 30 nucleotides long. In some embodiments, the level of transmission of the virus is determined by assessing the level of a marker of infection, including a virus structural protein, a virus nonstructural protein, a virus nucleic acid sequence, or combinations thereof.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 8A depicts representative FACS plots shown from one healthy donor. FIG. 8B depicts pooled data from 3 donors. The bar graph depicts mean±SE of percentage of dead cells in culture.

FIGS. 9A-9C, depicts the results of an example experiment demonstrating that an abasic 14-mer phosphorothioate 2' deoxyribose backbone (PDB) and OPB-T effectively inhibits replication and infection of cell-free HIV$_{IIIB}$ and HIV$_{BaL}$. (A) HIV$_{IIIB}$ inhibition by PDB and OPT-T is shown. (B) HIV$_{BaL}$ inhibition by PDB is shown. HIV was exposed for 30 minutes to 5 µM and 25 µM of PDB or OPB-T before the HIV-compound mixture was added to P4-R5 MAGI cells. β-gal expression was measured 48 hours later. (C) PDB inhibits infection of PBMC by HIV$_{BaL}$. Following exposure of HIV to 1 µM, 5 µM or 25 µM of PDB, the HIV/compound mixture was added to activated PBMC for 1 hour. P24 levels were measured in cell supernatants at 48 hours post-infection using a standard viral antigen ELISA.

FIGS. 11A-11C, depicts the results of an example experiment demonstrating that PDB induces no death in human PBMC or HEC-1-A cells exposed continuously to the compound for 24 hours. A continuous 24 hour exposure to PDB had no effect on the viability of resting or activated human PBMC. PBMC from healthy donors were either unstimulated (resting) or stimulated with 10 µg/ml PHA-P and 20 U/ml IL-2 (activated) for 48 hours. Cells were then harvested and resuspended in fresh RPMI 1840 with 10% FBS and treated with 25 µM and 250 µM PDB for 24 hours. Cells were harvested and stained with Annexin-V Cy5.5 and run on a FACSAria flow cytometer. Data was analyzed using FlowJo software. (A) Representative FACS plots shown from one healthy donor. (B) Pooled data from n=3 donors is shown. (C) A continuous 24 hour exposure of HEC-1-A cells to PDB at a concentration of 250 µM had no effect on their viability. Viability measured by MTT assay. Pooled data from n=3 experiments shown.

DETAILED DESCRIPTION

Figure 1:
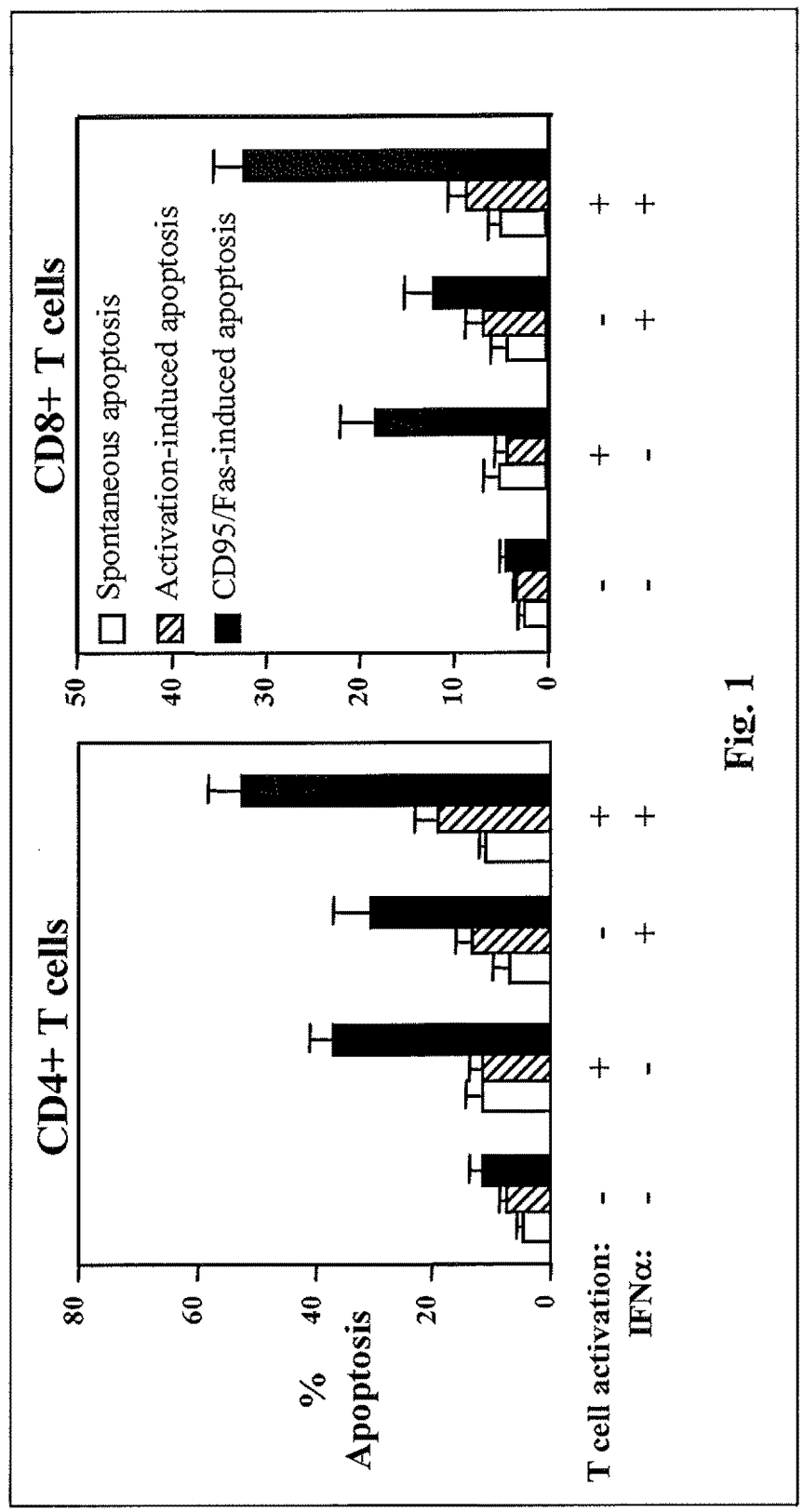
FIG. 1 depicts the results of an example experiment demonstrating that Type I interferons enhance CD95/Fas-induced T cell apoptosis. IFN-α (5 ng/mL) treatment of resting or activated T cells for 72 hours increases overnight CD95/Fas-induced apoptosis as measured by Annexin V staining and flow cytometry. T cells were activated with anti-CD3 antibody. n=5 healthy donors for each group.

The invention relates to compositions and methods for preventing and diminishing virus infection. The invention further relates to compositions and methods for diminishing inflammation associated with viral infection. The invention also relates to compositions and methods for interfering with TLR activation, and thereby diminishing inflammation associated with viral infection.

In one embodiment, viral infection is prevented or diminished by contacting a virus with a microbicide, such as, for example, a nucleic acid inhibitor or a phosphorothioate inhibitor. In various embodiments, the nucleic acid inhibitor of infection is DNA or RNA. In some embodiments, the nucleic acid inhibitor of infection can be a single-stranded or double-stranded nucleic acid. In some embodiments, the inhibitor of infection can be a baseless phosphorothioate backbone.

In another embodiment, the transmission of a virus to a cell is prevented or diminished by contacting the virus with a microbicide, such as, for example, a nucleic acid inhibitor or a phosphorothioate inhibitor. In various embodiments, the nucleic acid inhibitor is DNA or RNA. In some embodiments, the nucleic acid inhibitor of infection can be a single-stranded or double-stranded nucleic acid. In some embodiments, the inhibitor of infection can be a baseless phosphorothioate backbone.

In various embodiments, the virus infection prevented or diminished is caused by at least one of the group consisting of Human immunodeficiency virus, Simian immunodeficiency virus, Influenza A virus, Influenza B virus, Influenza C virus, Herpes virus, Hepatitis A virus, Hepatitis B virus, Hepatitis C virus, Hepatitis D virus, Adenovirus, Adeno-associated virus, Coronavirus, SARS coronavirus, Hantavirus, Respiratory syncytial virus and Papilloma virus.

In one embodiment, TLR activation is diminished by contacting the TLR with a nucleic acid inhibitor of the TLR activation. In various embodiments, the nucleic acid inhibitor of TLR activation is DNA or RNA or a phosphorothioate inhibitor. In some embodiments, the nucleic acid inhibitor of TLR activation can be single-stranded or double-stranded. In some embodiments, the inhibitor of infection can be a baseless phosphorothioate backbone. In one embodiment, the TLR is TLR7. In another embodiment, the TLR is TLR 8. In yet another embodiment, the TLR is TLR 9. In some embodiments, the TLR is combination of TLR7, TLR8 and TLR9.

In another embodiment, inflammation associated with viral infection is diminishes by diminishing TLR activation by contacting the TLR with a nucleic acid inhibitor. In various embodiments, the nucleic acid inhibitor of TLR activation is DNA or RNA or a phosphorothioate inhibitor. In some embodiments, the nucleic acid inhibitor of TLR activation can be single-stranded or double-stranded. In some embodiments, the inhibitor of infection can be a baseless phosphorothioate backbone. In one embodiment, the TLR is TLR7. In another embodiment, the TLR is TLR 8. In yet another embodiment, the TLR is TLR 9. In some embodiments, the TLR is combination of TLR7, TLR8 and TLR9.

In various embodiments, the inflammation is associated with a viral infection where the virus is one of the group consisting of Influenza A virus, Influenza B virus, Influenza C virus, Herpes virus, Hepatitis A virus, Hepatitis B virus, Hepatitis C virus, Hepatitis D virus, Human immunodeficiency virus, Simian immunodeficiency virus, Adenovirus, Adeno-associated virus, Coronavirus, SARS coronavirus, Hantavirus, Respiratory syncytial virus and Papilloma virus.

Nucleic Acids

Nucleic acids according to the present invention may include any polymer or oligomer of pyrimidine and purine bases, preferably cytosine, thymine, and uracil, and adenine and guanine, respectively. (See Albert L. Lehninger, Principles of Biochemistry, at 793-800). Indeed, the present invention contemplates any deoxyribonucleotide, ribonucleotide or peptide nucleic acid component, and any chemical modifications thereof, such as methylated, hydroxymethylated or glucosylated forms of these bases, and the like. The polymers or oligomers may be heterogeneous or homogeneous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex and hybrid states. By way of non-limiting examples, nucleic acids useful in the invention include sense nucleic acids, antisense nucleic acids, oligonucleotides, polynucleotides, double-stranded DNA, single-stranded DNA, double-stranded RNA and single-stranded RNA.

In various embodiments of the invention, the nucleic acid inhibitors of the invention, as well as other nucleic acids sharing all or some portion of the sequence of the nucleic acid inhibitors of the invention, can be administered to an individual to reduce inflammation associated with viral infection. In other embodiments of the invention, the nucleic acid inhibitors of the invention, as well as other nucleic acids sharing all or some portion of the sequence of the nucleic acid inhibitors of the invention, can be used to contact a virus to prevent or diminish transmission of the virus to a cell. By way of non-limiting examples, nucleic acid reference sequences, upon which the sequences of the nucleic acid inhibitors of the invention can be based, include, but are not limited to:

```
TTTTTTTTTTTTTTTTTTTTTTTTTTTTTT  (SEQ ID NO: 1)

AAAAAAAAAAAAAAAAAAAAAAAAAAAAAA  (SEQ ID NO: 2)

GGGGGGGGGGGGGGGGGGGGGGGGGGGGGG  (SEQ ID NO: 3)

CCCCCCCCCCCCCCCCCCCCCCCCCCCCCC  (SEQ ID NO: 4)

UUUUUUUUUUUUUUUUUUUUUUUUUUUUUU  (SEQ ID NO: 5)
```

It will be readily understood by one skilled in the art that the nucleic acid inhibitors of the invention, include not only those represented by the nucleic acid reference sequences provided herein as examples (i.e., SEQ ID NOS: 1-5), but also include fragments, modifications and variants, as elsewhere defined herein, of the example nucleic acid reference sequences provided herein. Fragments of the nucleic acid references sequences provided herein include those based on the nucleic acid references sequences but that are a subsequence of the nucleic acid reference sequence and that are 2, 3, 4, 5, 6, 7, 8, 9, 10, 11, 12, 13, 14, 15, 16, 17, 18, 19, 20, 21, 22, 23, 24, 25, 26, 27, 28 or 29 nucleotides in length.

Also included in the nucleic acid inhibitors of the invention are "baseless" backbone nucleic acid inhibitors with backbones that would be 2, 3, 4, 5, 6, 7, 8, 9, 10, 11, 12, 13, 14, 15, 16, 17, 18, 19, 20, 21, 22, 23, 24, 25, 26, 27, 28, 29 or 30 nucleotides in length but which contain no bases and thus no nucleotides. Also included in the nucleic acid inhibitors of the invention are "nearly baseless" backbone nucleic acid inhibitors with backbones that would be 2, 3, 4, 5, 6, 7, 8, 9, 10, 11, 12, 13, 14, 15, 16, 17, 18, 19, 20, 21, 22, 23, 24, 25, 26, 27, 28, 29 or 30 nucleotides in length but which contain one base, and thus one nucleotide, at either the 3' or the 5' end. The "baseless" and "nearly baseless" backbones can comprise any of the backbones described elsewhere herein, including any of the backbone modifications as described elsewhere herein.

Modifications of Nucleic Acids

Following the generation of the nucleic acid of the present invention, a skilled artisan will understand that the nucleic acid will have certain characteristics that can be modified to improve the nucleic acid as a therapeutic compound. The skilled artisan will also understand that any of the modifications described herein can also be made to modify the "baseless" and "nearly baseless" backbones, having one or more abasic sites, described elsewhere herein.

For example, the oligonucleotide may be further designed to resist degradation by modifying it to include phosphorothioate, or other linkages, methylphosphonate, sulfone, sulfate, ketyl, phosphorodithioate, phosphoramidate, phosphate esters, and the like (see, e.g., Agrwal et al., 1987 Tetrahedron Lett. 28:3539-3542; Stec et al., 1985 Tetrahedron Lett. 26:2191-2194; Moody et al., 1989 Nucleic Acids Res. 12:4769-4782; Eckstein, 1989 Trends Biol. Sci. 14:97-100; Stein, In: Oligodeoxynucleotides. Antisense Inhibitors of Gene Expression, Cohen, ed., Macmillan Press, London, pp. 97-117 (1989)).

Possible modifications include, but are not limited to, the addition of flanking sequences at the 5' and/or 3' ends; the use of phosphorothioate or 2' O-methyl rather than phosphodiester linkages in the backbone; and/or the inclusion of nontraditional bases such as inosine, queosine, and wybutosine and the like, as well as acetyl-methyl-, thio- and other modified forms of adenine, cytidine, guanine, thymine, and uridine, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo uracils and cytosines particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine (see U.S. Pat. No. 3,687,808; Englisch et al., 1991, Angewandte Chemie, International Edition; 30:613; Sanghvi, 1993, Chapter 15, Antisense Research and Applications, pages 289-302, CRC Press, 1993; Limbach et al., 1994, Nucleic Acids Res. 22:2183-2196; Rozenski et al., 1999, Nucleic Acids Res. 27:196-197).

The modification can, for example, improve pharmacokinetics or stability of a therapeutic nucleic acid agent. The universal bases described herein can be incorporated into the nucleic acid agents.

For increased nuclease resistance, the single-stranded nucleic acid agents featured in the invention can include 2'-O-methyl, 2'-fluorine, 2'-O-methoxyethyl, 2'-O-aminopropyl, 2'-amino, and/or phosphorothioate linkages. Inclusion of locked nucleic acids (LNA), ethylene nucleic acids (ENA), e.g., 2'-4'-ethylene-bridged nucleic acids, and certain nucleobase modifications such as 2-amino-A, 2-thio (e.g., 2-thio-U), G-clamp modifications, can also be made. The inclusion of pyranose sugars in the nucleic acid backbone can also decrease endonucleolytic cleavage. A nucleic acid can be further modified by including a 3' cationic group, or by inverting the nucleoside at the 3'-terminus with a 3'-3' linkage. In another alternative, the 3'-terminus can be blocked with an aminoalkyl group, e.g., a 3' C5-aminoalkyl dT. Other 3' conjugates can inhibit 3'-5' exonucleolytic cleavage. Even small alkyl chains, aryl groups, or heterocyclic conjugates or modified sugars (D-ribose, deoxyribose, glucose etc.) can block 3'-5'-exonucleases. The 5'-terminus can be blocked with an aminoalkyl group, e.g., a 5'-O-alkylamino substituent. Other 5' conjugates can inhibit 5'-3' exonucleolytic cleavage. Even small alkyl chains, aryl groups, or heterocyclic conjugates or modified sugars (D-ribose, deoxyribose, glucose etc.) can block 5'-3' exonucleases.

A nucleic acid, such as a single-stranded nucleic acid agent, featured in the invention can be constructed using chemical synthesis and/or enzymatic ligation reactions using procedures known in the art. For example, a nucleic acid can be chemically synthesized using naturally occurring nucleotides or variously modified nucleotides designed to increase the biological stability of the molecules or to increase the physical stability of the duplex formed between the nucleic acid and target nucleic acids, e.g., phosphorothioate derivatives and acridine substituted nucleotides can be used. Other appropriate nucleic acid modifications are described herein. Alternatively, the nucleic acid can be produced biologically using an expression vector into which a nucleic acid has been subcloned.

For ease of exposition the term nucleotide or ribonucleotide is sometimes used herein in reference to one or more monomeric subunits of a nucleic acid agent. It will be understood herein that the usage of the term "ribonucleotide" or "nucleotide" herein can, in the case of a modified RNA or nucleotide surrogate, also refer to a modified nucleotide, or surrogate replacement moiety at one or more positions.

Nucleic acid agents discussed herein include otherwise unmodified RNA and DNA as well as RNA and DNA that have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, preferably as occur naturally in the human body. The art has referred to rare or unusual, but naturally occurring, RNAs as modified RNAs, see, e.g., Limbach et al. (*Nucleic Acids Res.,* 1994, 22:2183-2196). Such rare or unusual RNAs, often termed modified RNAs, are typically the result of a post-transcriptional modification and are within the term unmodified RNA as used herein. Modified RNA, as used herein, refers to a molecule in which one or more of the components of the nucleic acid, namely sugars, bases, and phosphate moieties, are different from that which occur in nature, preferably different from that which occurs in the human body. While they are referred to as "modified RNAs" they will of course, because of the modification, include molecules that are not, strictly speaking, RNAs. Nucleoside surrogates are molecules in which the ribophosphate backbone is replaced with a non-ribophosphate construct that allows the bases to be presented in the correct spatial relationship such that hybridization is substantially similar to what is seen with a ribophosphate backbone, e.g., non-charged mimics of the ribophosphate backbone. Examples of all of the above are discussed herein.

As nucleic acids are polymers of subunits or monomers, many of the modifications described herein occur at a position which is repeated within a nucleic acid, e.g., a modification of a base, or a phosphate moiety, or a non-linking O of a phosphate moiety. In some cases the modification will occur at all of the subject positions in the nucleic acid but in many, and in fact in most cases it will not. By way of example, a modification may only, occur at a 3' or 5' terminal position, in a terminal region, e.g., at a position on a terminal nucleotide, or in the last 2, 3, 4, 5, or 10 nucleotides of a strand. For example, a phosphorothioate modification at a non-linking O position may only occur at one or both termini, or may only occur in a terminal region, e.g., at a position on a terminal nucleotide or in the last 2, 3, 4, 5, or 10 nucleotides of the nucleic acid. The 5' end can be phosphorylated.

The phosphate group is a negatively charged species. The charge is distributed equally over the two non-linking oxygen atoms. However, the phosphate group can be modified by replacing one of the oxygens with a different substituent. One result of this modification to RNA phosphate backbones can be increased resistance of the nucleic acid to nucleolytic breakdown. Thus while not wishing to be bound by theory, it can be desirable in some embodiments to introduce alterations which result in either an uncharged linker or a charged linker with unsymmetrical charge distribution.

Examples of modified phosphate groups include phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur. The phosphorus center in the phosphorodithioates is achiral which precludes the formation of oligoribonucleotides diastereomers. Diastereomer formation can result in a preparation, in which the individual diastereomers exhibit varying resistance to nucleases. Thus, while not wishing to be bound by theory, modifications which eliminate the chiral center, may be desirable in that they cannot produce diastereomer mixtures. The replacement can be made with any one of S, Se, B, C, H, N, or OR (R is alkyl or aryl).

The phosphate linker can also be modified by replacement of a linking oxygen with nitrogen (bridged phosphoroamidates), sulfur (bridged phosphorothioates) and carbon (bridged methylenephosphonates). The replacement can occur at a terminal oxygen.

A modified nucleic acid can include modification of all or some of the sugar groups of the ribonucleic acid. For example, the 2' hydroxyl group (OH) can be modified or replaced with a number of different "oxy" or "deoxy" substituents.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), $O(CH_2CH_2O)_nCH_2CH_2OR$; "locked" nucleic acids (LNA) in which the 2' hydroxyl is connected, e.g., by a methylene bridge or ethylene bridge (e.g., 2'-4'-ethylene bridged nucleic acid (ENA)), to the 4' carbon of the same ribose sugar; amino, O-AMINE (AMINE=$NH_2$; alkylamino, dialkylamino, heterocyclyl, arylamino, diaryl amino, heteroaryl amino, or diheteroaryl amino, ethylene diamine, polyamino) and aminoalkoxy, $O(CH_2)_n$AMINE, (e.g., AMINE=$NH_2$; alkylamino, dialkylamino, heterocyclyl, arylamino, diaryl amino, heteroaryl amino, or diheteroaryl amino, ethylene diamine, polyamino). It is noteworthy that nucleic acids containing only the methoxyethyl group (MOE), ($OCH_2CH_2OCH_3$, a PEG derivative), exhibit nuclease stabilities comparable to those modified with the robust phosphorothioate modification.

"Deoxy" modifications include hydrogen (i.e. deoxyribose sugars); halo (e.g., fluoro); amino (e.g. $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$; alkylamino, dialkylamino, heterocyclyl, arylamino, diaryl amino, heteroaryl amino, or diheteroaryl amino), —NHC(O)R (R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality. Preferred substitutents are 2'-methoxyethyl, 2'-$OCH_3$, 2'-O-allyl, 2'-C-allyl, and 2'-fluoro.

The sugar group can also contain one or more carbons that possess the opposite stereochemical configuration than that of the corresponding carbon in ribose. Thus, a modified RNA can include nucleotides containing e.g., arabinose, as the sugar.

Modified RNAs can also include "abase" sugars, which lack a nucleobase at C-1'. These abasic sugars can also further contain modifications at one or more of the constituent sugar atoms.

To maximize nuclease resistance, the 2' modifications can be used in combination with one or more phosphate linker modifications (e.g., phosphorothioate). The so-called "chimeric" nucleic acids are those that contain two or more different modifications.

The modification can also entail the wholesale replacement of a ribose structure with another entity (an SRMS) at one or more sites in the nucleic acid agent.

The phosphate group can be replaced by non-phosphorus containing connectors. While not wishing to be bound by theory, it is believed that since the charged phosphodiester group is the reaction center in nucleolytic degradation, its replacement with neutral structural mimics should impart enhanced nuclease stability. Again, while not wishing to be bound by theory, it can be desirable, in some embodiment, to introduce alterations in which the charged phosphate group is replaced by a neutral moiety. Examples of moieties which can replace the phosphate group include siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. Preferred replacements include the methylenecarbonylamino and methylenemethylimino groups.

Nucleic acid-mimicking scaffolds can also be constructed wherein the phosphate linker and ribose sugar are replaced by nuclease resistant nucleoside or nucleotide surrogates. While not wishing to be bound by theory, it is believed that the absence of a repetitively charged backbone diminishes binding to proteins that recognize polyanions (e.g. nucleases). Again, while not wishing to be bound by theory, it can be desirable in some embodiment, to introduce alterations in which the bases are tethered by a neutral surrogate backbone. Examples include the mophilino, cyclobutyl, pyrrolidine and peptide nucleic acid (PNA) nucleoside surrogates. A preferred surrogate is a PNA surrogate.

The 3' and 5' ends of a nucleic acid can be modified. Such modifications can be at the 3' end, 5' end or both ends of the molecule. They can include modification or replacement of an entire terminal phosphate or of one or more of the atoms of the phosphate group. E.g., the 3' and 5' ends of a nucleic acid can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a spacer. The terminal atom of the spacer can connect to or replace the linking atom of the phosphate group or the C-3' or C-5' O, N, S or C group of the sugar. Alternatively, the spacer can connect to or replace the terminal atom of a nucleotide surrogate (e.g., PNAs). These spacers or linkers can include e.g., —$(CH_2)_n$—, —$(CH_2)_n$N—, —$(CH_2)_n$O—, —$(CH_2)_n$S—, $O(CH_2CH_2O)_nCH_2CH_2OH$ (e.g., n=3 or 6), abasic sugars, amide, carboxy, amine, oxyamine, oxyimine, thioether, disulfide, thiourea, sulfonamide, or morpholino, or biotin and fluorescein reagents. While not wishing to be bound by theory, it is believed that conjugation of certain moieties can improve transport, hybridization, and specificity properties. Again, while not wishing to be bound by theory, it may be desirable to introduce terminal alterations that improve nuclease resistance. Other examples of terminal modifications include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic carriers (e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)litho-cholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles).

Terminal modifications can be added for a number of reasons, including as discussed elsewhere herein to modulate activity or to modulate resistance to degradation. Preferred modifications include the addition of a methylphosphonate at the 3'-most terminal linkage; a 3' C5-aminoalkyl-dT; 3' cationic group; or another 3' conjugate to inhibit 3'-5' exonucleolytic degradation.

Terminal modifications useful for modulating activity include modification of the 5' end with phosphate or phosphate analogs. E.g., in preferred embodiments nucleic acid agents are 5' phosphorylated or include a phosphoryl analog at the 5' terminus. 5'-phosphate modifications include those which are compatible with RISC mediated gene silencing. Suitable modifications include: 5'-monophosphate ((HO)2 (O)P—O-5'); 5'-diphosphate ((HO)2(O)P—O—P(HO) (O)—O-5'); 5'-triphosphate ((HO)2(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)2(S)P—O-5'); 5'-monodithiophosphate (phosphorodithioate; (HO)(HS) (S)P—O-5'), 5'-phosphorothiolate ((HO)2(O)P—S-5'); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates ((HO)2(O)P—NH-5', (HO)(NH2)(O)P—O-5'), 5'-alkylphosphonates (R=alkyl=methyl, ethyl, isopropyl, propyl, etc., e.g. RP(OH)(O)—O-5'-, (OH)2(O)P-5'-CH2-), 5'-alkyletherphosphonates (R=alkylether=methoxymethyl (MeOCH2-), ethoxymethyl, etc., e.g. RP(OH)(O)—O-5'-).

Terminal modifications can also be useful for monitoring distribution, and in such cases the preferred groups to be added include fluorophores, e.g., fluorscein or an Alexa dye, e.g., Alexa 488. Terminal modifications can also be useful for enhancing uptake, useful modifications for this include cholesterol. Terminal modifications can also be useful for cross-linking a nucleic acid to another moiety; modifications useful for this include mitomycin C.

Adenine, guanine, cytosine and uracil are the most common bases found in RNA. These bases can be modified or replaced to provide RNA's having improved properties. E.g., nuclease resistant oligoribonucleotides can be prepared with these bases or with synthetic and natural nucleobases (e.g., inosine, thymine, xanthine, hypoxanthine, nubularine, isoguanisine, or tubercidine) and any one of the above modifications. Alternatively, substituted or modified analogs of any of the above bases, e.g., "unusual bases" and "universal bases" described herein, can be employed. Examples include without limitation 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, N6,N6-dimethyladenine, 2,6-di-aminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3carboxypropyl)uracil, 3-methylcytosine, 5-methylcytosine, N$^4$-acetyl cytosine, 2-thiocytosine, N6-methyladenine, N6-isopentyladenine, 2-methylthio-N6-isopentenyladenine, N-methylguanines, or O-alkylated bases. Further purines and pyrimidines include those disclosed in U.S. Pat. No. 3,687,808, those disclosed in the Concise Encyclopedia Of Polymer Science And Engineering, pages 858-859, Kroschwitz, J. I., ed. John Wiley & Sons, 1990, and those disclosed by Englisch et al., Angewandte Chemie, International Edition, 1991, 30, 613.

One can evaluate a candidate single-stranded nucleic acid agent, e.g., a modified candidate single-stranded nucleic acid agent, for a selected property by exposing the agent or modified molecule and a control molecule to the appropriate conditions and evaluating for the presence of the selected property. For example, resistance to a degradent can be evaluated as follows. A candidate modified nucleic acid (and preferably a control single-stranded nucleic acid agent, usually the unmodified form) can be exposed to degradative conditions, e.g., exposed to a milieu, which includes a degradative agent, e.g., a nuclease. For example, one can use a biological sample, e.g., one that is similar to a milieu, which might be encountered, in therapeutic use, e.g., blood or a cellular fraction, e.g., a cell-free homogenate or disrupted cells. The candidate and control can then be evaluated for resistance to degradation by any of a number of approaches. For example, the candidate and control could be labeled, preferably prior to exposure, with, e.g., a radioactive or enzymatic label, or a fluorescent label, such as Cy3 or Cy5. Control and modified nucleic acid agents can be incubated with the degradative agent, and optionally a control, e.g., an inactivated, e.g., heat inactivated, degradative agent. A physical parameter, e.g., size, of the modified and control molecules are then determined. They can be determined by a physical method, e.g., by polyacrylamide gel electrophoresis or a sizing column, to assess whether the molecule has maintained its original length, or assessed functionally. Alternatively, Northern blot analysis can be used to assay the length of an unlabeled modified molecule.

A functional assay can also be used to evaluate the candidate agent. A functional assay can be applied initially or after an earlier non-functional assay, (e.g., assay for resistance to degradation) to determine if the modification alters the ability of the molecule to interfere with the transmission of a virus or to inhibit TLR activation. Efficacy of the candidate agent on inhibition of virus transmission can be assessed by comparing virus transmission in the presence of the modified and unmodified nucleic acid agent. Efficacy of the candidate agent on inhibition of TLR activation can be assessed by comparing TLR activation in the presence of the modified and unmodified nucleic acid agent.

A nucleic acid, such as, for example, a single-stranded nucleic acid agent, featured in the invention can have enhanced resistance to nucleases. For increased nuclease resistance and/or binding affinity to the target, a nucleic acid agent can include, for example, 2'-modified ribose units and/or phosphorothioate linkages. E.g., the 2' hydroxyl group (OH) can be modified or replaced with a number of different "oxy" or "deoxy" substituents.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), $O(CH_2CH_2O)_nCH_2CH_2OR$; "locked" nucleic acids (LNA) in which the 2' hydroxyl is connected, e.g., by a methylene bridge, to the 4' carbon of the same ribose sugar; amine, O-AMINE and aminoalkoxy, $O(CH_2)_n$AMINE, (e.g., AMINE=$NH_2$; alkylamino, dialkylamino, heterocyclyl amino, arylamino, diaryl amino, heteroaryl amino, or diheteroaryl amino, ethylene diamine, polyamino). It is noteworthy that nucleic acids containing only the methoxyethyl group (MOE), ($OCH_2CH_2OCH_3$, a PEG derivative), exhibit nuclease stabilities comparable to those modified with the robust phosphorothioate modification.

"Deoxy" modifications include hydrogen (i.e. deoxyribose sugars); halo (e.g., fluoro); amino (e.g. $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$; alkylamino, dialkylamino, heterocyclyl amino, arylamino, diaryl amino, heteroaryl amino, or diheteroaryl amino), —NHC(O)R (R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality.

One way to increase resistance is to identify cleavage sites and modify such sites to inhibit cleavage. For example, the dinucleotides 5'-UA-3', 5'-UG-3', 5'-CA-3', 5'-UU-3', or 5'-CC-3' can serve as cleavage sites. Enhanced nuclease resistance can therefore be achieved by modifying the 5' nucleotide, resulting, for example, in at least one 5'-uridine-adenine-3' (5'-UA-3') dinucleotide wherein the uridine is a 2'-modified nucleotide; at least one 5'-uridine-guanine-3' (5'-UG-3') dinucleotide, wherein the 5'-uridine is a 2'-modified nucleotide; at least one 5'-cytidine-adenine-3' (5'-CA-3') dinucleotide, wherein the 5'-cytidine is a 2'-modified nucleotide; at least one 5'-uridine-uridine-3' (5'-UU-3') dinucleotide, wherein the 5'-uridine is a 2'-modified nucleotide; or at least one 5'-cytidine-cytidine-3' (5'-CC-3') dinucleotide, wherein the 5'-cytidine is a 2'-modified nucleotide. The nucleic acid can include at least 2, at least 3, at least 4 or at least 5 of such dinucleotides. In certain embodiments, all the pyrimidines of a nucleic acid carry a 2'-modification, and the nucleic acid therefore has enhanced resistance to endonucleases.

To maximize nuclease resistance, the 2' modifications can be used in combination with one or more phosphate linker modifications (e.g., phosphorothioate). The so-called "chimeric" nucleic acids are those that contain two or more different modifications.

The inclusion of furanose sugars in the nucleic acid backbone can also decrease endonucleolytic cleavage. A nucleic acid can be further modified by including a 3' cationic group, or by inverting the nucleoside at the 3'-terminus with a 3'-3' linkage. In another alternative, the 3'-terminus can be blocked with an aminoalkyl group, e.g., a 3' C5-aminoalkyl dT. Other 3' conjugates can inhibit 3'-5' exonucleolytic cleavage. While not being bound by theory, a 3' conjugate, such as naproxen or ibuprofen, may inhibit exonucleolytic cleavage by sterically blocking the exonuclease from binding to the 3'-end of nucleic acid. Even small alkyl chains, aryl groups, or heterocyclic conjugates or modified sugars (D-ribose, deoxyribose, glucose etc.) can block 3'-5'-exonucleases.

Similarly, 5' conjugates can inhibit 5'-3' exonucleolytic cleavage. While not being bound by theory, a 5' conjugate may inhibit exonucleolytic cleavage by sterically blocking the exonuclease from binding to the 5'-end of the nucleic acid. Even small alkyl chains, aryl groups, or heterocyclic conjugates or modified sugars (D-ribose, deoxyribose, glucose etc.) can block 5'-3'-exonucleases.

Thus, a nucleic acid can include modifications so as to inhibit degradation, e.g., by nucleases, e.g., endonucleases or exonucleases, found in the body of a subject. In many cases these modifications will modulate other properties of the nucleic acid as well, e.g., the ability to interact with a protein, e.g., a transport protein, e.g., serum albumin, or a member of the RISC, or the ability of the nucleic acid to form a complex with a target molecule, such as a TLR.

One or more different modifications can be introduced into a nucleic acid or into a sequence of a nucleic acid agent. A modification can be used more than once in a sequence or in a nucleic acid agent.

Modifications include some which can be placed only at the terminus and others which can go at any position. Some modifications that can inhibit hybridization are preferably used only in terminal regions, and more preferably not at the cleavage site or in the cleavage region of the nucleic acid agent.

Modifications which interfere with or inhibit endonuclease cleavage should not be inserted in the region which is subject to RISC mediated cleavage, e.g., the cleavage site or the cleavage region (As described in Elbashir et al., *Genes and Dev.* 15:188, 2001, hereby incorporated by reference). Cleavage of the target occurs about in the middle of a 20 or 21 nucleotide nucleic acid agent, or about 10 or 11 nucleotides upstream of the first nucleotide on the target mRNA which is complementary to the nucleic acid agent. As used herein, cleavage site refers to the nucleotides on either side of the site of cleavage, on the target mRNA or on the nucleic acid which hybridizes to it. Cleavage region means the nucleotides within 1, 2, or 3 nucleotides of the cleavage site, in either direction.

Such modifications can be introduced into the terminal regions, e.g., at the terminal position or with 2, 3, 4, or 5 positions of the terminus, of a sequence which targets or a sequence which does not target a sequence in the subject.

Assays

The present invention has application in various assays, including, assays for determining whether a particular nucleic acid inhibitor or a baseless phosphorothioate inhibitor is an inhibitor of TLR activation, whether a particular nucleic acid inhibitor or a baseless phosphorothioate inhibitor can diminish inflammation associated with viral infection, and whether a particular nucleic acid or a baseless phosphorothioate inhibitor can interfere with the transmission of a virus.

Biological samples useful in the methods of the invention can be any biological fluid, cell, tissue, or a biological fluid-, cell- or tissue-containing composition or isolate. Thus, the diagnostic method of the invention comprises measuring the amount or level of a marker of inflammation or the amount or level of a marker of infection. A marker of inflammation useful in the method of the invention can include, for example, a cytokine or, for example, a particular type of immune cell. A marker of infection useful in the method of the invention can include any viral component able to be detected, including a viral structural protein, a viral nonstructural protein, or a viral nucleic acid sequence. The amount or level of the marker of inflammation, or the marker of infection, present in the biological sample can then be compared to the amount or level in one or more standards or comparators. By way of non-limiting examples, standards and/or comparators can include, a biological sample derived from an individual known not to be infected by a virus and a biological sample derived from an individual known to be infected by a virus. By way of a further non-limiting example, standards and/or comparators useful in the invention can include negative controls and historical norms or averages.

Methods of detecting and measuring the amount of a marker of inflammation or infection present in a biological sample are well known in the art. The practice of the present invention may employ, unless otherwise indicated, conventional techniques and descriptions of organic chemistry, polymer technology, molecular biology (including recombinant techniques), cell biology, biochemistry and immunology, which are within the skill of the art. Such conventional techniques include polymer array synthesis, hybridization, ligation, and detection of hybridization using a label. Specific illustrations of suitable techniques can be had by reference to the examples herein below. However, other equivalent conventional procedures can, of course, also be used. Such conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press); Stryer, L., 1995, Biochemistry (4th Ed.) Freeman, New York; Gait, 1984, "Oligonucleotide Synthesis: A Practical Approach," IRL Press, London, Nelson and Cox; Lehninger, Principles of Biochemistry 3rd Ed., W.H. Freeman Pub., New York, N.Y.; Berg et al., 2002, Biochemistry, 5th Ed., W.H. Freeman Pub., New York, N.Y., Nolan et al., 2006, Nat. Protoc. 1:1559-1582, Higuchi et al, 1993, Biotechnology 11:1026-1030, and Mackay, 2007, Real-Time PCR in Microbiology, Norwich, U.K., all of which are herein incorporated in their entirety by reference for all purposes.

The present invention also contemplates sample preparation and quantitation methods in certain embodiments. Prior to or concurrent with analysis, the biological sample may be amplified using a variety of mechanisms, some of which may employ PCR and/or RT-PCR. See, for example, PCR Technology: Principles and Applications for DNA Amplification (Ed. H. A. Erlich, Freeman Press, NY, N.Y., 1992); PCR Protocols: A Guide to Methods and Applications (Eds. Innis, et al., Academic Press, San Diego, Calif., 1990); Mattila et al., Nucleic Acids Res. 19, 4967 (1991); Eckert et al., PCR Methods and Applications 1, 17 (1991); PCR (Eds. McPherson et al., IRL Press, Oxford); and U.S. Pat. Nos. 4,683,202, 4,683,195, 4,800,159 4,965,188, and 5,333,675, each of which is incorporated herein by reference in their entireties for all purposes.

Other suitable amplification methods include the ligase chain reaction (LCR) (for example, Wu and Wallace, Genomics 4, 560 (1989); Landegren et al., Science 241, 1077 (1988) and Barringer et al. Gene 89:117 (1990)), transcription amplification (Kwoh et al., Proc. Natl. Acad. Sci. USA 86, 1173 (1989) and WO88/10315), self-sustained sequence replication (Guatelli et al., Proc. Nat. Acad. Sci. USA, 87, 1874 (1990) and WO90/06995), selective amplification of target polynucleotide sequences (U.S. Pat. No. 6,410,276), consensus sequence primed PCR (CP-PCR) (U.S. Pat. No. 4,437,975), arbitrarily primed PCR (AP-PCR) (U.S. Pat. Nos. 5,413,909, 5,861,245), degenerate nucleic acid primed PCR (DOP-PCR) (Wells et al., 1999, Nuc Acids Res 27:1214-1218) and nucleic acid based sequence amplification (NABSA). (See, U.S. Pat. Nos. 5,409,818, 5,554,517, and 6,063,603, each of which is incorporated herein by reference). Other amplification methods that may be used are described in, U.S. Pat. Nos. 5,242,794, 5,494,810, 4,988,617 and in U.S. Ser. No. 09/854,317, each of which is incorporated herein by reference.

Additional methods of sample preparation and techniques for reducing the complexity of a nucleic sample are described in Dong et al., Genome Research 11, 1418 (2001), in U.S. Pat. Nos. 6,361,947, 6,391,592 and U.S. Ser. Nos. 09/916,135, 09/920,491 (US Patent Application Publication 20030096235), Ser. No. 09/910,292 (US Patent Application Publication 20030082543), and Ser. No. 10/013,598.

Methods for conducting nucleic acid hybridization assays, for example, but not limited to southern blots, northern blots and microarrays, have been developed in the art. Hybridization assay procedures and conditions will vary depending on the application and are selected in accordance with the general binding methods known including those referred to in: Sambrook et al. (2001, Molecular Cloning: A Laboratory Manual, Cold Spring Harbor Laboratory, New York); Berger and Kimmel Methods in Enzymology, Vol. 152, Guide to Molecular Cloning Techniques (Academic Press, Inc., San Diego, Calif., 1987); Young and Davism, P.N.A.S, 80:1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference. Nucleic acid arrays that are useful in the present invention include arrays such as those commercially available from Invitrogen (Santa Clara, Calif.) (example arrays and methods are shown on the website at www.invitrogen.com).

It is also contemplated that the hybridized nucleic acids can be detected by detecting one or more labels attached to the sample nucleic acids. The labels may be incorporated by any of a number of means well known to those of skill in the art. In one embodiment, the label is simultaneously incorporated during the amplification step in the preparation of the sample nucleic acids. Thus, for example, PCR with labeled primers or labeled nucleotides will provide a labeled amplification product. In another embodiment, transcription amplification, as described above, using a labeled nucleotide (e.g. fluorescein-labeled UTP and/or CTP) incorporates a label into the transcribed nucleic acids. In another embodiment PCR amplification products are fragmented and labeled by terminal deoxytransferase and labeled dNTPs. Alternatively, a label may be added directly to the original nucleic acid sample (e.g., mRNA, polyA mRNA, cDNA, etc.) or to the amplification product after the amplification is completed. Means of attaching labels to nucleic acids are well known to those of skill in the art and include, for example, nick translation or end-labeling (e.g. with a labeled RNA) by kinasing the nucleic acid and subsequent attachment (ligation) of a nucleic acid linker joining the sample nucleic acid to a label (e.g., a fluorophore). In another embodiment label is added to the end of fragments using terminal deoxytransferase.

Detectable labels suitable for use in the present invention include any composition detectable by spectroscopic, photochemical, biochemical, immunochemical, electrical, optical or chemical means. Useful labels in the present invention include, but are not limited to: biotin for staining with labeled streptavidin conjugate; anti-biotin antibodies, magnetic beads (e.g., Dynabeads™); fluorescent dyes (e.g., fluorescein, texas red, rhodamine, green fluorescent protein, and the like); radiolabels (e.g., $^3$H, $^{125}$I, $^{35}$S, $^{4}$C, or $^{32}$P); phosphorescent labels; enzymes (e.g., horse radish peroxidase, alkaline phosphatase and others commonly used in an ELISA); and colorimetric labels such as colloidal gold or colored glass or plastic (e.g., polystyrene, polypropylene, latex, etc.) beads. Patents teaching the use of such labels include U.S. Pat. Nos. 3,817,837, 3,850,752, 3,939,350, 3,996,345, 4,277,437, 4,275,149 and 4,366,241, each of which is hereby incorporated by reference in its entirety for all purposes.

Means of detecting such labels are well known to those of skill in the art. Thus, for example, radiolabels may be detected using photographic film or scintillation counters; fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label.

Antibodies

As will be understood by one skilled in the art, any antibody that can recognize and specifically bind to a marker of inflammation, or a marker of infection, is useful in the present invention. Markers of inflammation include, for example, but are not limited to, cytokines and other cell-derived mediators of inflammation, as well as the presence, number and differentiation state of particular immune cell mediators of inflammation. The skilled artisan will understand that a marker of inflammation is any measurable characteristic of an inflammatory immune response. Markers of infection included, for example, viral structural proteins, viral non-structural proteins, and viral nucleic acid sequences. The skilled artisan will understand that a marker of infection is any measurable characteristic of virus infection. The invention should not be construed to be limited to any one type of antibody, either known or heretofor unknown. Methods of making and using such antibodies are well known in the art. For example, the generation of polyclonal antibodies can be accomplished by inoculating the desired individual with the antigen and isolating antibodies which specifically bind the antigen therefrom. Monoclonal antibodies directed against full length or peptide fragments of a protein or peptide may be prepared using any well known monoclonal antibody preparation procedures, such as those described, for example, in Harlow et al. (1999, Using Antibodies: A Laboratory Manual, Cold Spring Harbor Laboratory Press, N.Y.), Harlow et al. (1989, Antibodies: A Laboratory Manual, Cold Spring Harbor, N.Y.) and in Tuszynski et al (1988, Blood 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein. However, the invention should not be construed as being limited solely to methods and compositions including these antibodies, but should be construed to include other antibodies, as that term is defined elsewhere herein, or portions thereof.

One of skill in the art will further appreciate that the present invention encompasses the use of antibodies derived from camelid species. That is, the present invention includes, but is not limited to, the use of antibodies derived from species of the camelid family. As is well known in the art, camelid antibodies differ from those of most other mammals in that they lack a light chain, and thus comprise only heavy chains with complete and diverse antigen binding capabilities (Hamers-Casterman et al., 1993, Nature 363:446-448). Such heavy-chain antibodies are useful in that they are smaller than conventional mammalian antibodies, they are more soluble than conventional antibodies, and further demonstrate an increased stability compared to some other antibodies.

Camelid species include, but are not limited to Old World camelids, such as two-humped camels (*C. bactrianus*) and one humped camels (*C. dromedarius*). The camelid family further comprises New World camelids including, but not limited to llamas, alpacas, vicuna and guanaco. The use of Old World and New World camelids for the production of antibodies is contemplated in the present invention, as are other methods for the production of camelid antibodies set forth herein.

The production of polyclonal sera from camelid species is substantively similar to the production of polyclonal sera from other animals such as sheep, donkeys, goats, horses, rabbits, mice, chickens, rats, and the like. The skilled artisan can prepare high-titers of antibodies from a camelid species with no undue experimentation. As an example, the production of antibodies in mammals is detailed in such references as Harlow et al. (1999, Using Antibodies: A Laboratory Manual, Cold Spring Harbor Laboratory Press, New York) and Harlow et al. (1989, Antibodies: A Laboratory Manual, Cold Spring Harbor, N.Y.). Camelid species for the production of antibodies and sundry other uses are available from various sources, including but not limited to, Camello Fataga S.L. (Gran Canaria, Canary Islands) for Old World camelids, and High Acres Llamas (Fredricksburg, Tex.) for New World camelids.

The isolation of camelid antibodies from the serum of a camelid species, like the isolation of antibodies from the serum of other animals such as sheep, donkeys, goats, horses, rabbits, mice, chickens, rats, and the like, can be performed by many methods well known in the art, including but not limited to ammonium sulfate precipitation, antigen affinity purification, Protein A and Protein G purification, and the like. As an example, a camelid species may be immunized to a desired antigen or fragment thereof, using techniques well known in the art. The whole blood can them be drawn from the camelid and sera can be separated using standard techniques. The sera can then be absorbed onto a Protein G-Sepharose column (Pharmacia, Piscataway, N.J.) and washed with appropriate buffers, for example 20 mM phosphate buffer (pH 7.0). The camelid antibody can then be eluted using a variety of techniques well known in the art, for example 0.15M NaCl, 0.58% acetic acid (pH 3.5). The efficiency of the elution and purification of the camelid antibody can be determined by various methods, including SDS-PAGE, Bradford Assays, and the like. The fraction that is not absorbed can be bound to a Protein A-Sepharose column (Pharmacia, Piscataway, N.J.) and eluted using, for example 0.15M NaCl, 0.58% acetic acid (pH 4.5). The skilled artisan will readily understand that the above methods for the isolation and purification of camelid antibodies are exemplary, and other methods for protein isolation are well known in the art and are encompassed in the present invention.

The present invention further contemplates the production of camelid antibodies expressed from nucleic acid. Such methods are well known in the art, and are detailed in, for example U.S. Pat. Nos. 5,800,988; 5,759,808; 5,840,526, and 6,015,695, which are incorporated herein by reference in their entirety. Briefly, cDNA can be synthesized from camelid spleen mRNA. Isolation of RNA can be performed using multiple methods and compositions, including TRIZOL (Gibco/BRL, La Jolla, Calif.) further, total RNA can be isolated from tissues using the guanidium isothiocyanate method detailed in, for example, Sambrook et al. (2001, Molecular Cloning, A Laboratory Manual, Cold Spring Harbor, N.Y.). Methods for purification of mRNA from total cellular or tissue RNA are well known in the art, and include, for example, oligo-T paramagnetic beads. cDNA synthesis can then be obtained from mRNA using mRNA template, an oligo dT primer and a reverse transcriptase enzyme, available commercially from a variety of sources, including Invitrogen (La Jolla, Calif.). Second strand cDNA can be obtained from mRNA using RNAse hr and *E. coli* DNA polymerase I according to techniques well known in the art.

Identification of cDNA sequences of relevance can be performed by hybridization techniques well known by one of ordinary skill in the art, and include methods such as Southern blotting, RNA protection assays, and the like. Probes to identify variable heavy immunoglobulin chains ($V_{HH}$) are available commercially and are well known in the art, as detailed in, for example, Sastry et al. (1989, Proc. Nat'l. Acad. Sci. USA 86:5728). Full-length clones can be produced from cDNA sequences using any techniques well known in the art and detailed in, for example, Sambrook et al. (2001, Molecular Cloning, A Laboratory Manual, Cold Spring Harbor, N.Y.).

The clones can be expressed in any type of expression vector known to the skilled artisan. Further, various expression systems can be used to express the $V_{HH}$ peptides of the present invention, and include, but are not limited to eukaryotic and prokaryotic systems, including bacterial cells, mammalian cells, insect cells, yeast cells, and the like. Such methods for the expression of a protein are well known in the art and are detailed elsewhere herein.

The $V_{HH}$ immunoglobulin proteins isolated from a camelid species or expressed from nucleic acids encoding such proteins can be used directly in the methods of the present invention, or can be further isolated and/or purified using methods disclosed elsewhere herein.

The present invention is not limited to $V_{HH}$ proteins isolated from camelid species, but also includes $V_{HH}$ proteins isolated from other sources such as animals with heavy chain disease (Seligmann et al., 1979, Immunological Rev. 48:145-167, incorporated herein by reference in its entirety). The present invention further comprises variable heavy chain immunoglobulins produced from mice and other mammals, as detailed in Ward et al. (1989, Nature 341:544-546, incorporated herein by reference in its entirety). Briefly, $V_H$ genes were isolated from mouse splenic preparations and expressed in *E. coli*. The present invention encompasses the use of such heavy chain immunoglobulins in the treatment of various autoimmune disorders detailed herein, expression of $V_H$ (variable heavy chain immunoglobulin) genes from an animal.

Nucleic acid encoding the monoclonal antibody obtained using the procedures described herein may be cloned and sequenced using technology which is available in the art, and is described, for example, in Wright et al. (1992, Critical Rev. in Immunol. 12:125-168) and the references cited therein. Further, the antibody of the invention may be "humanized" using the technology described in Wright et al. (supra) and in the references cited therein, and in Gu et at (1997, Thrombosis and Hematocyst 77:755-759).

To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (2001, Molecular Cloning: A Laboratory Manual, Cold Spring Harbor, N.Y.).

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art and are described for example, in Wright et al. (supra).

Processes such as those described above, have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al. (1991, J. Mol. Biol. 222: 581-597). Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839; de Kruif et al., 1995, J. Mol. Biol. 248:97-105).

Immunoassays

A variety of immunoassay formats, including competitive and non-competitive immunoassay formats, antigen capture assays, two-antibody sandwich assays, and three-antibody sandwich assays are useful methods of the invention (Self et al., 1996, Curr. Opin. Biotechnol. 7:60-65). The invention should not be construed to be limited to any one type of known or heretofore unknown immunoassay, provided that the immunoassay is able to evaluate and/or measure the level of inflammation associated with virus infection.

In one embodiment, the method of the invention relies on one or more antigen capture assays. In one such antigen capture assay, antibody is bound to a solid support, and sample is added such that the antigen-of-interest is bound by the antibody. After unbound proteins are removed by washing, the amount of bound antigen-of-interest can be quantified, if desired, using, for example, but not limited to, a radioassay (Harlow et al., 1999, Using Antibodies: A Laboratory Manual, Cold Spring Harbor Laboratory Press, New York; and Harlow et al., 1989, Antibodies: A Laboratory Manual, Cold Spring Harbor, N.Y.).

Enzyme-linked immunosorbent assays (ELISAs) are useful in the methods of the invention. An enzyme such as, but not limited to, horseradish peroxidase (HRP), alkaline phosphatase (AP), beta-galactosidase or urease can be linked, for example, to an antibody or to a secondary antibody for use in a method of the invention. A horseradish-peroxidase detection system may be used, for example, with the chromogenic substrate tetramethylbenzidine (TMB), which yields a soluble product in the presence of hydrogen peroxide that is detectable at 450 nm. Other convenient enzyme-linked systems include, for example, the alkaline phosphatase detection system, which may be used with the chromogenic substrate p-nitrophenyl phosphate to yield a soluble product readily detectable at 405 nm. Similarly, a beta-galactosidase detection system may be used with the chromogenic substrate o-nitrophenyl-beta-D-galactopyranoside (ONPG) to yield a soluble product detectable at 410 nm. Alternatively, a urease detection system may be used with a substrate such as urea-bromocresol purple (Sigma Immunochemicals, St. Louis, Mo.). Useful enzyme-linked primary and secondary antibodies can be obtained from any number of commercial sources.

Chemiluminescent detection is also useful for detecting an antigen-of-interest, such as a marker of inflammation. Chemiluminescent secondary antibodies may be obtained from any number of commercial sources.

Fluorescent detection is also useful for detecting an antigen-of-interest, such as a marker of inflammation, or for determining a level of an antigen-of-interest, such as a marker of inflammation, in a method of the invention. Useful fluorochromes include, but are not limited to, DAPI, fluorescein, Hoechst 33258, R-phycocyanin, B-phycoerythrin, R-phycoerythrin, rhodamine, Texas red and lissamine-Fluorescein- or rhodamine-labeled antigen-specific antibodies.

Radioimmunoassays (RIAs) are also useful in the methods of the invention. Such assays are well known in the art, and are described for example in Brophy et al. (1990, Biochem. Biophys, Res. Comm. 167:898-903) and Guechot et al. (1996, Clin. Chem. 42:558-563). Radioimmunoassays are performed, for example, using Iodine-125-labeled primary or secondary antibody (Harlow et al., 1999, Using Antibodies: A Laboratory Manual, Cold Spring Harbor Laboratory Press, New York; Harlow et al., 1989, Antibodies: A Laboratory Manual, Cold Spring Harbor, N.Y.).

A signal emitted from a detectable antibody is analyzed, for example, using a spectrophotometer to detect color from a chromogenic substrate; a radiation counter to detect radiation, such as a gamma counter for detection of Iodine-125; or a fluorometer to detect fluorescence in the presence of light of a certain wavelength. Where an enzyme-linked assay is used, quantitative analysis of the amount of an antigen-of-interest is performed using a spectrophotometer. It is understood that the assays of the invention can be performed manually or, if desired, can be automated and that the signal emitted from multiple samples can be detected simultaneously in many systems available commercially.

The methods of the invention also encompass the use of capillary electrophoresis based immunoassays (CEIA), which can be automated, if desired. Immunoassays also may be used in conjunction with laser-induced fluorescence as described, for example, in Schmalzing et al. (1997, Electrophoresis 18:2184-2193) and Bao (1997, J, Chromatogr. B, Biomed. Sci. 699:463-480). Liposome immunoassays, such as flow-injection liposome immunoassays and liposome immunosensors, may also be used to detect an antigen-of-interest according to the methods of the invention (Rongen et al., 1997, J. Immunol. Methods 204:105-133).

Sandwich enzyme immunoassays may also be useful in the methods of the invention. In a two-antibody sandwich assay, a first antibody is bound to a solid support, and the antigen is allowed to bind to the first antibody. The amount of an antigen-of-interest is quantified by detecting and measuring the amount of a detectable second antibody that binds to the complex of the antigen and the first antibody. In a three-antibody sandwich assay, a first antibody is bound to a solid support, and the antigen is allowed to bind to the first antibody. Then a second antibody is added and is allowed to bind to the antigen, which is bound to the first antibody. The amount of antigen is quantified by detecting and measuring the amount of a detectable third antibody that binds to the second antibody.

Quantitative western blotting may also be used to detect an antigen-of-interest or to determine a level of an antigen-of-interest in a method of the invention. Western blots are quantified using well known methods such as scanning densitometry (Parra et al., 1998, J. Vase. Surg. 28:669-675).

Fluorescence activated cell sorting (FACS) analysis may also be used to detect an antigen-of-interest, for example a marker of inflammation on the surface of an immune cell, or to determine the level of antigen in a method of the invention. Using FACS analysis, cells may be stained with one or more fluorescent dyes specific to cell components of interest, including markers of inflammation, and fluorescence of each cell is measured as it rapidly transverses the excitation beam (laser or mercury arc lamp). The skilled artisan will understand that FACS analysis provides a quantitative measure of various biochemical and biophysical properties of a cell, or a population of cells, as well as a basis for cell sorting. The skilled artisan will understand that FACS analysis also provides a quantitative measure of the proportion of cells in a population of cells sharing a particular characteristic. Other measurable optical parameters include light absorption and light scattering, the latter being applicable to the measurement of cell size, shape, density, granularity, and stain uptake (see Darzynkiewicz et al., 2004, Cytometry (4th ed), Academic Press, Burlington, Mass.).

Vectors

In other related aspects, the invention includes an isolated nucleic acid encoding a nucleic acid inhibitor, such as, for example, a sense nucleic acid, an antisense nucleic acid, a polynucleotide, or a nucleic acid, wherein the isolated nucleic acid encoding the nucleic acid inhibitor is operably linked to a nucleic acid comprising a promoter/regulatory sequence. Thus, the invention encompasses expression vectors and methods for the introduction of exogenous DNA into cells with concomitant expression of the exogenous DNA in the cells such as those described, for example, in Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

In another aspect, the invention includes a vector comprising an polynucleotide. Preferably, the polynucleotide is capable of inhibiting TLR activation or virus transmission. The incorporation of a desired nucleic acid into a vector and the choice of vectors is well-known in the art as described in, for example, Sambrook et al., supra, and Ausubel et al., supra.

The nucleic acid inhibitor of the invention can be cloned into a number of types of vectors. However, the present invention should not be construed to be limited to any particular vector. Instead, the present invention should be construed to encompass a wide plethora of vectors which are readily available and/or well-known in the art. For example, the nucleic acid inhibitor of the invention can be cloned into a vector including, but not limited to a plasmid, a phagemid, a phage derivative, an animal virus and a cosmid. Vectors of particular interest include expression vectors, replication vectors, probe generation vectors and sequencing vectors.

In specific embodiments, the expression vector is selected from the group consisting of a viral vector, a bacterial vector and a mammalian cell vector. Numerous expression vector systems exist that comprise at least a part or all of the compositions discussed above. Prokaryote- and/or eukaryote-vector based systems can be employed for use with the present invention to produce polynucleotides. Many such systems are commercially and widely available.

Further, the expression vector may be provided to a cell in the form of a viral vector. Viral vector technology is well known in the art and is described, for example, in Sambrook et al. (2001), and in Ausubel et al. (1997), and in other virology and molecular biology manuals. Viruses, which are useful as vectors include, but are not limited to, retroviruses, adenoviruses, adeno-associated viruses, herpes viruses and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193.

For expression of the nucleic acid inhibitor of the invention, at least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 genes, a discrete element overlying the start site itself helps to fix the place of initiation.

Additional promoter elements, i.e., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either co-operatively or independently to activate transcription.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters, or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR in connection with the compositions disclosed herein (U.S. Pat. No. 4,683,202, U.S. Pat. No. 5,928,906). Furthermore, it is contemplated that control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle and organism chosen for expression. Those of skill in the art of molecular biology generally know how to use promoters, enhancers and cell type combinations for protein expression, for example, see Sambrook et al. (2001). The promoters employed may be constitutive, tissue-specific, inducible and/or useful under the appropriate conditions to direct high level expression of the introduced DNA segment, such as is advantageous in the large-scale production of recombinant proteins and/or peptides. The promoter may be heterologous or endogenous.

A promoter sequence exemplified in the experimental examples presented herein is the cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, Moloney virus promoter, the avian leukemia virus promoter, Epstein-Barr virus immediate early promoter, Rous sarcoma virus promoter, as well as human gene promoters such as, but not limited to, the actin promoter, the myosin promoter, the hemoglobin promoter, and the muscle creatine promoter. Further, the invention should not be limited to the use of constitutive promoters. Inducible promoters are also contemplated as part of the invention. The use of an inducible promoter in the invention provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. Further, the invention includes the use of a tissue specific promoter, which promoter is active only in a desired tissue. Tissue specific promoters are well known in the art and include, but are not limited to, the HER-2 promoter and the PSA associated promoter sequences.

In order to assess the expression of the nucleic acid inhibitor of the invention, the expression vector to be introduced, into a cell can also contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. Expression of the reporter gene is assayed, at a suitable time after the DNA has been introduced into the recipient cells.

Suitable reporter genes may include genes encoding luciferase, beta-galactosidase, chloramphenicol acetyl transferase, secreted alkaline phosphatase, or the green fluorescent protein gene (see, e.g., Ui-Tei et al., 2000 FEBS Lett. 479: 79-82). Suitable expression systems are well known and may be prepared using well known techniques or obtained commercially. Internal deletion constructs may be generated using unique internal restriction sites or by partial digestion of non-unique restriction sites. Constructs may then be transfected into cells. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of Treatment

The methods of the invention comprise administering a therapeutically effective amount of at least one nucleic acid inhibitor or a baseless phosphorothioate inhibitor, to a cell, or to an individual with a viral infection, or to an individual identified as having a viral infection, where the nucleic acid inhibitor or a baseless phosphorothioate inhibitor of TLR activation reduces, diminishes or decreases the level of TLR activation and the level and/or severity of inflammation associated with viral infection. The methods of the invention also comprise administering a therapeutically effective amount of at least one nucleic acid inhibitor or a baseless phosphorothioate inhibitor, to a virus, to a cell, or to an individual in need of avoiding a viral infection, where the nucleic acid inhibitor of virus infection reduces, diminishes or decreases the level of transmission of the virus to the cell or to the individual.

The methods of the present invention may be practiced on any individual identified as having a viral infection, or on any individual in need of avoiding a viral infection. In a preferred embodiment the individual is a mammal. In a more preferred embodiment the individual is a human.

The present invention should in no way be construed to be limited to the inhibitors described herein, but rather should be construed to encompass any nucleic inhibitor or nucleic acid modified backbone inhibitor of viral infection or TLR activation, both known and unknown, that diminishes the level of transmission of the virus, or diminishes the level of TLR activation and inflammation associated with viral infection.

The methods of the invention comprise administering a therapeutically effective amount of at least one nucleic acid inhibitor or a baseless phosphorothioate inhibitor of TLR activation to an individual wherein the nucleic acid inhibitor or baseless phosphorothioate inhibitor of TLR activation, or a combination thereof prevents, attenuates, reduces or diminishes TLR activation, and/or that prevents, attenuates, reduces or diminishes the level or severity of inflammation associated with viral infection.

The methods of the invention comprise administering a therapeutically effective amount of at least one nucleic acid inhibitor or a baseless phosphorothioate inhibitor of TLR activation to an individual wherein the nucleic acid inhibitor of TLR activation, or a combination thereof, is used either alone or in combination with other therapeutic agents. The invention can be used in combination with other anti-viral treatment modalities, as well as with other anti-inflammation treatment modalities.

Nucleic acid inhibitors of the invention can be delivered to a cell in vitro or in vivo using vectors comprising one or more isolated inhibitor nucleic acid sequences. In some embodiments, the nucleic acid sequence has been incorporated into the genome of the vector. The vector comprising a nucleic acid inhibitor described herein can be contacted with a cell in vitro or in vivo and infection or transfection can occur. The cell can then be used experimentally to study, for example, the effect of a nucleic acid inhibitor in vitro. The cell can be present in a biological sample obtained from an individual (e.g., blood, bone marrow, tissue, biological fluids, organs, etc.) and used in the treatment of disease, or can be obtained from cell culture.

Various vectors can be used to introduce an isolated nucleic acid inhibitor into animal cells. Examples of viral vectors have been discussed elsewhere herein and include retrovirus, adenovirus, parvovirus (e.g., adeno-associated viruses), coronavirus, negative-strand RNA viruses such as orthomyxovirus (e.g., influenza virus), rhabdovirus (e.g., rabies and vesicular stomatitis virus), paramyxovirus (e.g. measles and Sendai), positive-strand RNA viruses such as picornavirus and alphavirus, and double stranded DNA viruses including adenovirus, herpesvirus (e.g., herpes simplex virus types 1 and 2, Epstein-Barr virus, cytomegalovirus), and poxvirus (e.g. vaccinia, fowlpox and canarypox). Other viruses include Norwalk virus, togavirus, flavivirus reoviruses, papovavirus, hepadnavirus and hepatitis virus, for example. Examples of retroviruses include: avian leukosis-sarcoma, mammalian C-type, B-type viruses, D-type viruses, HTLV-BLV group, lentivirus (e.g. human immunodeficiency virus), and spumavirus (Coffin, J. M., Retroviridae: The viruses and their replication, In Fundamental Virology, Third Edition, B. N. Fields et al., Eds.; Lippincott-Raven Publishers, Philadelphia, 1996). Other examples include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus, lentiviruses and baculoviruses.

In addition, an engineered viral vector can be used to deliver an isolated nucleic acid inhibitor of the present invention. These vectors provide a means to introduce nucleic acids into cycling and quiescent cells, and have been modified to reduce cytotoxicity and to improve genetic stability. The preparation and use of engineered Herpes simplex virus type 1 (Krisky et al., 1997, Gene Therapy 4:1120-1125), adenoviral (Amalfitanl et al., 1998, Journal of Virology 72:926-933) attenuated lentiviral (Zufferey et al., 1997, Nature Biotechnology 15:871-875) and adenoviral/retroviral chimeric (Feng et at, 1997, Nature Biotechnology 15:866-870) vectors are known to the skilled artisan.

In addition to delivery through the use of vectors, a nucleic acid inhibitor can be delivered to cells without vectors, e.g. as "naked" nucleic acid delivery using methods known to those of skill in the art. See, for example, U.S. Pat. Nos. 5,350,674 and 5,585,362. Physical methods for introducing a nucleic acid into a host cell include transfection, calcium phosphate precipitation, lipofection, particle bombardment, microinjection, electroporation and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York), and in Ausubel et al. (2001, Current Protocols in Molecular Biology, John Wiley & Sons, New York).

Chemical means for introducing a nucleic acid inhibitor into a host cell include colloidal dispersion systems, such as macromolecule complexes, nanocapsules, microspheres, beads, and lipid-based systems including oil-in-water emulsions, micelles, mixed micelles and liposomes. A preferred colloidal system for use as a delivery vehicle in vitro and in vivo is a liposome (i.e., an artificial membrane vesicle). The preparation and use of such systems is well known in the art.

Various forms of a nucleic acid inhibitor, as described herein, can be administered or delivered to an animal cell (e.g., by virus, direct injection, or liposomes, or by any other suitable methods known in the art or later developed). The methods of delivery can be modified to target certain cells, and in particular, cell surface receptor molecules. As an example, the use of cationic lipids as a carrier for nucleic acid constructs provides an efficient means of delivering the nucleic acid inhibitor of the present invention.

Various formulations of cationic lipids have been used to deliver nucleic acids to cells (WO 91/17424; WO 91/16024; U.S. Pat. Nos. 4,897,355; 4,946,787; 5,049,386; and 5,208,036). Cationic lipids have also been used to introduce foreign nucleic acids into frog and rat cells in vivo (Holt et al., *Neuron* 4:203-214 (1990); Hazinski et al., *Am. J. Respr. Cell. Mol. Biol.* 4:206-209 (1991)). Therefore, cationic lipids may be used, generally, as pharmaceutical carriers to provide biologically active substances (for example, see WO 91/17424; WO 91/16024; and WO 93/03709). Thus, cationic liposomes can provide an efficient carrier for the introduction of nucleic acids into a cell.

Further, liposomes can be used as carriers to deliver a nucleic acid or a baseless phosphorothioate inhibitor to a cell, tissue or organ. Liposomes comprising neutral or anionic lipids do not generally fuse with the target cell surface, but are taken up phagocytically, and the nucleic acids are subsequently subjected to the degradative enzymes of the lysosomal compartment (Straubinger et al., 1983, *Methods Enzymol.* 101:512-527; Mannino et al., 1988, *Biotechniques* 6:682-690). However, an isolated nucleic acid of the present invention can be a stable nucleic acid, and thus, may not be susceptible to degradative enzymes. Further, despite the fact that the aqueous space of typical liposomes may be too small to accommodate large macromolecules, the isolated nucleic acid inhibitor or baseless phosphorothioate inhibitor of the present invention is relatively small, and therefore, liposomes are a suitable delivery vehicle for the present invention. Methods of delivering a nucleic acid to a cell, tissue or organism, including liposome-mediated delivery, are known in the art and are described in, for example, Feigner (Gene Transfer and Expression Protocols Vol. 7, Murray, E. J. Ed., Humana Press, New Jersey, (1991)).

In other related aspects, the invention includes an isolated nucleic acid inhibitor operably linked to a nucleic acid comprising a promoter/regulatory sequence such that the nucleic acid is preferably capable of delivering a nucleic acid inhibitor. Thus, the invention encompasses expression vectors and methods for the introduction of an isolated nucleic acid inhibitor into or to cells.

Such delivery can be accomplished by generating a plasmid, viral, or other type of vector comprising an isolated nucleic acid inhibitor operably linked to a promoter/regulatory sequence which serves to introduce the nucleic acid inhibitor into cells in which the vector is introduced. Many promoter/regulatory sequences useful for the methods of the present invention are available in the art and include, but are not limited to, for example, the cytomegalovirus immediate early promoter enhancer sequence, the SV40 early promoter, as well as the Rous sarcoma virus promoter, and the like. Moreover, inducible and tissue specific expression of an isolated nucleic acid inhibitor may be accomplished by placing an isolated nucleic acid inhibitor, with or without a tag, under the control of an inducible or tissue specific promoter/regulatory sequence. Examples of tissue specific or inducible promoter/regulatory sequences which are useful for his purpose include, but are not limited to the MMTV LTR inducible promoter, and the SV40 late enhancer/promoter. In addition, promoters which are well known in the art which are induced in response to inducing agents such as metals, glucocorticoids, and the like, are also contemplated in the invention. Thus, it will be appreciated that the invention includes the use of any promoter/regulatory sequence, which is either known or unknown, and which is capable of driving expression of the desired protein operably linked thereto.

Selection of any particular plasmid vector or other vector is not a limiting factor in the invention and a wide plethora of vectors are well-known in the art. Further, it is well within the skill of the artisan to choose particular promoter/regulatory sequences and operably link those promoter/regulatory sequences to a DNA sequence encoding a desired polypeptide. Such technology is well known in the art and is described, for example, in Sambrook et al. (2001, Molecular Cloning: A Laboratory Manual, Cold Spring Harbor Laboratory, New York), and in Ausubel et al. (2001, Current Protocols in Molecular Biology, John Wiley & Sons, New York) and elsewhere herein.

Pharmaceutical Compositions and Therapies

Administration of a nucleic acid inhibitor of the invention comprising one or more nucleic acids, antisense nucleic acids, polynucleotides, or oligonucleotides of the invention in a method of treatment can be achieved in a number of different ways, using methods known in the art. Such methods include, but are not limited to, providing exogenous nucleic acids, antisense nucleic acids, polynucleotides, or oligonucleotides to a subject or expressing a recombinant nucleic acid, antisense nucleic acid, polynucleotide, or oligonucleotide expression cassette.

The therapeutic and prophylactic methods of the invention thus encompass the use of pharmaceutical compositions comprising a nucleic acid inhibitor, including at least one of an antisense nucleic acid, a polynucleotide, or an oligonucleotide or a baseless phosphorothioate inhibitor. The pharmaceutical compositions useful for practicing the invention may be administered to deliver a dose of between 1 ng/kg/day and 100 mg/kg/day. In one embodiment, the invention envisions administration of a dose which results in a concentration of the compound of the present invention between 1 µM and 10 µM in a mammal. In another embodiment, the invention envisions administration of a dose which results in a concentration of the compound of the present invention between 1 µM and 10 µM in a cell of a mammal.

Typically, dosages which may be administered in a method of the invention to an individual, preferably a human, range in amount from 0.5 µg to about 50 mg per kilogram of body weight of the animal. While the precise dosage administered will vary depending upon any number of factors, including but not limited to, the type of individual and type of disease state being treated, the age of the individual and the route of administration. Preferably, the dosage of the compound will vary from about 1 µg to about 10 mg per kilogram of body weight of the animal. More preferably, the dosage will vary from about 3 µg to about 1 mg per kilogram of body weight of the animal.

The nucleic acid inhibitor or baseless phosphorothioate inhibitor of the invention may be administered to an individual, or to a part of an individual such as a cell of an animal, as frequently as several times daily, or it may be administered less frequently, such as once a day, once a week, once every two weeks, once a month or even less frequently, such as once every several months or even once a year or less. The frequency of the dose will be readily apparent to the skilled artisan and will depend upon any number of factors, such as, but not limited to, the type and severity of the disease being treated, the type and age of the individual, etc. The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the description of pharmaceutical compositions provided herein are principally directed to pharmaceutical compositions which are suitable for ethical administration to humans, it will be understood by the skilled artisan that such compositions are generally suitable for administration to animals of all sorts, including mammals and birds. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, birds, humans and other primates, mammals including commercially relevant mammals such as non-human primates, cattle, pigs, horses, sheep, cats, and dogs.

Pharmaceutical compositions that are useful in the methods of the invention may be prepared, packaged, or sold in formulations suitable for ophthalmic, oral, rectal, vaginal, parenteral, topical, pulmonary, intranasal, buccal, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. A unit dose is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents.

Controlled- or sustained-release formulations of a pharmaceutical composition of the invention may be made using conventional technology.

Parenteral administration of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intraocular, intravitreal, subcutaneous, intraperitoneal, intramuscular, intrasternal injection, and intratumoral.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, creams, lotions, gels, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

Formulations of a pharmaceutical composition suitable for topical (including mucosal) administration comprise the active ingredient combined with a pharmaceutically acceptable carrier, such as sterile water or sterile isotonic saline. Such formulations may be prepared, packaged, or sold in a form suitable for bolus administration or for continuous administration. Formulations may be prepared, packaged, or sold in unit dosage form, such as in ampules or in multi-dose containers containing a preservative. Formulations for topical administration include, but are not limited to, suspensions, solutions, emulsions in oily or aqueous vehicles, pastes, creams, lotions, gels, and implantable sustained-release or biodegradable formulations. Such formulations may further comprise one or more additional ingredients including, but not limited to, suspending, stabilizing, or dispersing agents. In one embodiment of a formulation for topical administration, the active ingredient is provided in dry (i.e. powder or granular) form for reconstitution with a suitable vehicle (e.g. sterile pyrogen-free water) prior to administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention. Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

Pharmaceutical compositions of the invention formulated for intravaginal or intrarectal delivery may also provide the active ingredient in the form of gels, hydrogels, creams, solutions or suspensions. Gels and hydrogels may include but not limited to HydroxyEthyl Cellulose (HEC) gel, alginate gels or other gels or hydrogels suitable for vaginal or rectal application. Such formulations may be prepared, packaged, or sold as gels, hydrogels, creams, solutions, suspensions, optionally sterile, comprising the active ingredient, and may conveniently be administered using any suitable applicator device. Such formulations may further comprise one or more additional ingredients including, but not limited to, a flavoring agent such as saccharin sodium, a buffering agent, a surface active agent, or a preservative such as sorbic acid or methylhydroxybenzoate.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences (1985, Genaro, ed., Mack Publishing Co., Easton, Pa.), which is incorporated herein by reference.

Kits

The invention also includes a kit comprising a nucleic acid inhibitor or a baseless phosphorothioate inhibitor, or combinations thereof, of the invention and an instructional material which describes, for instance, administering the nucleic acid inhibitor or a baseless phosphorothioate inhibitor, or a combinations thereof, to a subject as a therapeutic treatment or a non-treatment use as described elsewhere herein. In an embodiment, this kit further comprises a (preferably sterile) pharmaceutically acceptable carrier suitable for dissolving or suspending the therapeutic composition, comprising a nucleic acid inhibitor or a baseless phosphorothioate inhibitor, or combinations thereof, of the invention, for instance, prior to administering the molecule to a subject. Optionally, the kit comprises an applicator for administering the inhibitor.

Definitions

The definitions used in this application are for illustrative purposes and do not limit the scope of the invention.

The articles "a" and "an" are used herein to refer to one or to more than one (i.e. to at least one) of the grammatical object of the article. By way of example, "an element" means one element or more than one element.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)2, as well as single chain antibodies and humanized antibodies (Harlow et al., 1999, Using Antibodies: A Laboratory Manual, Cold Spring Harbor Laboratory Press, New York; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

"Antisense nucleic acid" as used herein means a non-enzymatic nucleic acid molecule that binds to target nucleic acid molecule by means of RNA-RNA or RNA-DNA or RNA-PNA (protein nucleic acid; Egholm et al., 1993 Nature 365, 566) interactions and alters the activity of the target nucleic acid (for a review, see Stein and Cheng, 1993 Science 261, 1004 and Woolf et al., U.S. Pat. No. 5,849,902). Typically, antisense molecules are complementary to a target sequence along a single contiguous sequence of the antisense molecule. However, an antisense molecule can also bind to substrate such that the substrate molecule forms a loop, and/or an antisense molecule can bind such that the antisense molecule forms a loop. Thus, the antisense molecule can be complementary to two (or even more) non-contiguous substrate sequences or two (or even more) non-contiguous sequence portions of an antisense molecule can be complementary to a target sequence or both. In addition, antisense DNA can be used to target RNA by means of DNA-RNA interactions, thereby activating RNaseH, which digests the target RNA in the duplex. The antisense nucleic acids can comprise one or more RNAseH activating region, which is capable of activating RNaseH cleavage of a target RNA. Antisense DNA can be synthesized chemically or expressed via the use of a single stranded DNA expression vector or equivalent thereof.

"Complementary" as used herein refers to the broad concept of subunit sequence complementarity between two nucleic acids. When a nucleotide position in both of the molecules is occupied by nucleotides normally capable of base pairing with each other, then the nucleic acids are considered to be complementary to each other at this position. Thus, two nucleic acids are substantially complementary to each other when at least about 50%, preferably at least about 60% and more preferably at least about 80% of corresponding positions in each of the molecules are occupied by nucleotides which normally base pair with each other (e.g., A:T and G:C nucleotide pairs).

The terms "diminish" and "diminution," as used herein, means to reduce, suppress, inhibit or block an activity or function by at least about 10% relative to a comparator value. Preferably, the activity is suppressed, inhibited or blocked by 50% compared to a comparator value, more preferably by 75%, and even more preferably by 95%.

The terms "baseless backbone" and "nearly baseless backbone," as used herein, are used to mean a nucleic acid molecule where all (i.e., baseless) or nearly all (i.e., nearly baseless) of the positions of the backbone of the nucleic acid molecule are abasic (i.e., lack a nucleobase (e.g., purines and pyrimidines)). Nearly baseless backbones include backbones having only one base, as well as backbones having a few, or several bases.

The term "downstream" when used in reference to a direction along a nucleotide sequence means the 5'→3' direction. Similarly, the term "upstream" means the 3'→5' direction.

The terms "effective amount" and "pharmaceutically effective amount" refer to a nontoxic but sufficient amount of an agent to provide the desired biological result. That result can be reduction and/or alleviation of the signs, symptoms, or causes of a disease or disorder, or any other desired alteration of a biological system. An appropriate effective amount in any individual case may be determined by one of ordinary skill in the art using routine experimentation.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

By "expression cassette" is meant a nucleic acid molecule comprising a coding sequence operably linked to promoter/regulatory sequences necessary for transcription and, optionally, translation of the coding sequence.

The term "expression vector" as used herein refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules, polynucleotides or oligonucleotides, and the like. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well.

"Fragment" as the term is used herein, is a nucleic acid that differs in length (for example, in the number of nucleotides) from the length of a reference nucleic acid, but retains essential properties of the reference nucleic acid molecule. One example of a retained essential property would be the ability of the fragment nucleic acid to bind to a particular target (e.g., a TLR, such as TLR7, or TLR 8, or TLR9) much like the reference nucleic acid sequence, and thereby inhibit TLR activation and inflammation associated with viral infection. Another example of a retained essential property would be the ability of the fragment nucleic acid to interfere with the transmission of a virus to a cell. A fragment of a nucleic acid can be a naturally occurring or can be a fragment that is not known to occur naturally. Non-naturally occurring fragments of nucleic acids may be made by mutagenesis techniques or by direct synthesis. Preferably, the fragment is at least about 25% of the length of the reference nucleic acid sequence. More preferably, the fragment is at least about 35% of the length of the reference nucleic acid sequence. Even more preferably, the fragment is at least about 45% of the length of the reference nucleic acid sequence.

As used herein, the term "heavy chain antibody" or "heavy chain antibodies" comprises immunoglobulin molecules derived from camelid species, either by immunization with an antigen and subsequent isolation of sera, or by the cloning and expression of nucleic acid sequences encoding such antibodies. The term "heavy chain antibody" or "heavy chain antibodies" further encompasses immunoglobulin molecules isolated from an animal with heavy chain disease, or prepared by the cloning and expression of $V_H$ (variable heavy chain immunoglobulin) genes from an animal.

As used herein, "homologous" refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity." In addition, when the term "homology" is used herein to refer to the nucleic acids and proteins, it should be construed to be applied to homology at both the nucleic acid and the amino acid levels. The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example, at the National Center for Biotechnology Information (NCBI) world wide web site having the universal resource locator www.ncbi.nlm.nih.gov/BLAST/. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (id.) and relationships between molecules which share a common pattern. When utilizing BLAST, Gapped BLAST, PSI-Blast, and PHI-Blast programs, the default parameters of the respective programs (e.g., XBLAST and NBLAST) can be used. See www.ncbi.nlm.nih.gov. The percent identity between two sequences can be determined using techniques similar to those described above, with or without allowing gaps. In calculating percent identity, typically exact matches are counted.

As used herein, "hybridization," "hybridize(s)" or "capable of hybridizing" is understood to mean the forming of a double or triple stranded molecule or a molecule with partial double or triple stranded nature. Complementary sequences in the nucleic acids pair with each other to form a double helix. The resulting double-stranded nucleic acid is a "hybrid." Hybridization may be between, for example two complementary or partially complementary sequences. The hybrid may have double-stranded regions and single stranded regions. The hybrid may be, for example, DNA:DNA, RNA:DNA or DNA:RNA. Hybrids may also be formed between modified nucleic acids. One or both of the nucleic acids may be immobilized on a solid support. Hybridization techniques may be used to detect and isolate specific sequences, measure homology, or define other characteristics of one or both strands. The stability of a hybrid depends on a variety of factors including the length of complementarity, the presence of mismatches within the complementary region, the temperature and the concentration of salt in the reaction. Hybridizations are usually performed under stringent conditions, for example, at a salt concentration of no more than 1 M and a temperature of at least 25.degree.C. For example, conditions of 5.times.SSPE (750 mM NaCl, 50 mM Na Phosphate, 5 mM EDTA, pH 7.4) or 100 mM MES, 1 M Na, 20 mM EDTA, 0.01% Tween-20 and a temperature of 25-50.degree.C. are suitable for allele-specific probe hybridizations. In a particularly preferred embodiment, hybridizations are performed at 40-50.degree.C. Acetylated BSA and herring sperm DNA may be added to hybridization reactions. Hybridization conditions suitable for microarrays are described in the Gene Expression Technical Manual and the GeneChip Mapping Assay Manual available from Affymetrix (Santa Clara, Calif.).

"Hybridization probes" are oligonucleotides capable of binding in a base-specific manner to a complementary strand of nucleic acid. Such probes include peptide nucleic acids, as described in Nielsen et al., 1991, Science 254, 1497-1500, and other nucleic acid analogs and nucleic acid mimetics. See U.S. Pat. No. 6,156,501.

An "individual," as that term is used herein, includes a member of any animal species able to be infected by a virus. Such animal species include, but are not limited to, birds, humans and other primates, and other mammals including commercially relevant mammals such as cattle, pigs, horses, sheep, cats, and dogs.

An "inducible" promoter is a nucleotide sequence which, when operably linked with a polynucleotide which encodes or specifies a gene product, causes the gene product to be produced substantially only when an inducer which corresponds to the promoter is present.

"Instructional material," as that term is used herein, includes a publication, a recording, a diagram, or any other medium of expression which can be used to communicate the usefulness of the composition and/or compound of the invention in a kit. The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

"Isolated" means altered or removed from the natural state through the actions of a human being. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "label" as used herein refers to a luminescent label, a light scattering label or a radioactive label. Fluorescent labels include, but are not limited to, the commercially available fluorescein phosphoramidites such as Fluoreprime (Pharmacia), Fluoredite (Millipore) and FAM (ABI). See U.S. Pat. No. 6,287,778.

By "modification" is meant any alteration of any nucleic acid of the invention to increase its stability in vivo. Possible modifications include, but are not limited to, the addition of flanking sequences at the 5' and/or 3' ends; the removal of terminal sequences at the 5' and/or 3' ends; the use of phosphorothioate or 2'-O-methyl rather than phosphodiester linkages in the backbone; and/or the inclusion of nontraditional bases such as inosine, queosine, and wybutosine and the like, as well as acetyl-methyl-, thio- and other modified forms of adenine, cytidine, guanine, thymine, and uridine. Other modifications known in the art will be readily understood by the skilled artisan to be included herein.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

An "oligonucleotide" or "polynucleotide" is a nucleic acid ranging from at least 2, and preferably at least 8, 15 or 25 nucleotides in length, but may be up to 50, 100, 1000, or 5000 nucleotides long or a compound that specifically hybridizes to a polynucleotide. Oligonucleotides of the present invention include sequences of deoxyribonucleic acid (DNA) or ribonucleic acid (RNA) or mimetics thereof which may be isolated from natural sources, recombinantly Produced or artificially synthesized. A further example of a polynucleotide of the present invention may be a peptide nucleic acid (PNA), (See U.S. Pat. No. 6,156,501 which is hereby incorporated by reference in its entirety.) The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this disclosure.

As used herein a "probe" is defined as a nucleic acid capable of binding to a target nucleic acid of complementary sequence through one or more types of chemical bonds, usually through complementary base pairing, usually through hydrogen bond formation. As used herein, a probe may include natural (i.e. A, G, U, C, or T) or modified bases (7-deazaguanosine, inosine, etc.). In addition, a linkage other than a phosphodiester bond may join the bases in probes, so long as it does not interfere with hybridization. Thus, probes may be peptide nucleic acids in which the constituent bases are joined by peptide bonds rather than phosphodiester linkages.

A "probe target pair" is formed when two macromolecules have combined through molecular recognition to form a complex.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in an inducible manner.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

By the term "specifically bind" or "specifically binds," as used herein, is meant that a first molecule (e.g., an antibody) preferentially binds to a second molecule (e.g., a particular antigenic epitope), but does not necessarily bind only to that second molecule.

The term "synthetic antibody," as used herein, refers to an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "target" as used herein refers to a molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Examples of targets which can be employed by the invention include, but are not restricted to, oligonucleotides, nucleic acids, antibodies, cell membrane receptors, monoclonal antibodies and antisera reactive with specific antigenic determinants (such as on viruses, cells or other materials), drugs, peptides, cofactors, lectins, sugars, polysaccharides, cells, cellular membranes, and organelles.

Targets are sometimes referred to in the art as anti-probes. As the term targets is used herein, no difference in meaning is intended.

"Variant" as the term is used herein, is a nucleic acid sequence that differs in sequence from a reference nucleic acid sequence, but retains essential properties of the reference molecule. One example of a retained essential property would be the ability of the variant nucleic acid to bind to a particular target (e.g., a TLR, such as TLR7, or TLR8, or TLR9) much like the reference nucleic acid sequence, and thereby inhibit TLR activation and inflammation associated with viral infection. Another example of a retained essential property would be the ability of the variant nucleic acid to interfere with the transmission of a virus to a cell. A variant of a nucleic acid can be a naturally occurring such as an allelic variant, or can be a variant that is not known to occur naturally. Non-naturally occurring variants of nucleic acids may be made by mutagenesis techniques or by direct synthesis. Preferably, the variant shares at least about 80% homology with the reference nucleic acid sequence. More preferably, the variant shares at least about 90% homology with the reference nucleic acid sequence. Even More preferably, the variant shares at least about 95% homology with the reference nucleic acid sequence.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, poly-1-lysine compounds, liposomes, and the like. Examples of viral vectors include, but are not limited to, adenoviral vectors, adeno-associated virus vectors, retroviral vectors, and the like.

The term "halo" refers to any radical of fluorine, chlorine, bromine or iodine.

The term "alkyl" refers to a hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. The term "haloalkyl" refers to an alkyl in which one or more hydrogen atoms are replaced by halo, and includes alkyl moieties in which all hydrogens have been replaced by halo (e.g., perfluoroalkyl). Alkyl and haloalkyl groups may be optionally inserted with O, N, or S. The terms "aralkyl" refers to an alkyl moiety in which an alkyl hydrogen atom is replaced by an aryl group. Aralkyl includes groups in which more than one hydrogen atom has been replaced by an aryl group. Examples of "aralkyl" include benzyl, 9-fluorenyl, benzhydryl, and trityl groups.

The term "alkenyl" refers to a straight or branched hydrocarbon chain containing 2-8 carbon atoms and characterized in having one or more double bonds. Examples of a typical alkenyl include; but not limited to, allyl, propenyl, 2-butenyl, 3-hexenyl and 3-octenyl groups. The term "alkynyl" refers to a straight or branched hydrocarbon chain containing 2-8 carbon atoms and characterized in having one or more triple bonds. Some examples of a typical alkynyl are ethynyl, 2-propynyl, and 3-methylbutynyl, and propargyl. The $sp^2$ and $sp^3$ carbons may optionally serve as the point of attachment of the alkenyl and alkynyl groups, respectively.

The terms "alkylamino" and "dialkylamino" refer to —NH(alkyl) and —NH(alkyl)$_2$ radicals respectively. The term "aralkylmino" refers to a —NH(aralkyl) radical. The term "alkoxy" refers to an —O-alkyl radical, and the terms "cycloalkoxy" and "aralkoxy" refer to an —O-cycloalkyl and O-aralkyl radicals respectively. The term "siloxy" refers to a $R_3SiO$— radical. The term "mercapto" refers to an SH radical. The term "thioalkoxy" refers to an —S-alkyl radical.

The term "alkylene" refers to a divalent alkyl (i.e., —R—), e.g., —CH$_2$—, —CH$_2$CH$_2$—, and —CH$_2$CH$_2$CH$_2$—. The term "alkylenedioxo" refers to a divalent species of the structure —O—R—O—, in which R represents an alkylene.

The term "aryl" refers to an aromatic monocyclic, bicyclic, or tricyclic hydrocarbon ring system, wherein any ring atom can be substituted. Examples of aryl moieties include, but are not limited to, phenyl, naphthyl, anthracenyl, and pyrenyl.

The term "cycloalkyl" as employed herein includes saturated cyclic, bicyclic, tricyclic, or polycyclic hydrocarbon groups having 3 to 12 carbons, wherein any ring atom can be substituted. The cycloalkyl groups herein described may also contain fused rings. Fused rings are rings that share a common carbon-carbon bond or a common carbon atom (e.g., spiro-fused rings). Examples of cycloalkyl moieties include, but are not limited to, cyclohexyl, adamantyl, and norbornyl, and decalin.

The term "heterocyclyl" refers to a nonaromatic 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom can be substituted. The heterocyclyl groups herein described may also contain fused rings. Fused rings are rings that share a common carbon-carbon bond or a common carbon atom (e.g., spiro-fused rings). Examples of heterocyclyl include, but are not limited to tetrahydrofuranyl, tetrahydropyranyl, piperidinyl, morpholino, pyrrolinyl and pyrrolidinyl.

The term "cycloalkenyl" as employed herein includes partially unsaturated, nonaromatic, cyclic, bicyclic, tricyclic, or polycyclic hydrocarbon groups having 5 to 12 carbons, preferably 5 to 8 carbons, wherein any ring atom can be substituted. The cycloalkenyl groups herein described may also contain fused rings. Fused rings are rings that share a common carbon-carbon bond or a common carbon atom (e.g., spiro-fused rings). Examples of cycloalkenyl moieties include, but are not limited to cyclohexenyl, cyclohexadienyl, or norbornenyl.

The term "heterocycloalkenyl" refers to a partially saturated, nonaromatic 5-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom can be substituted. The heterocycloalkenyl groups herein described may also contain fused rings. Fused rings are rings that share a common carbon-carbon bond or a common carbon atom (e.g., spiro-fused rings). Examples of heterocycloalkenyl include but are not limited to tetrahydropyridyl and dihydropyran.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicycle, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom can be substituted. The heteroaryl groups herein described may, also contain fused rings that share a common carbon-carbon bond.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The term "substituents" refers to a group "substituted" on an alkyl, cycloalkyl, alkenyl, alkynyl, heterocyclyl, heterocycloalkenyl, cycloalkenyl, aryl, or heteroaryl group at any atom of that group. Suitable substituents include, without limitation, alkyl, alkenyl, alkynyl, alkoxy, halo, hydroxy, cyano, nitro, amino, $SO_3H$, sulfate, phosphate, perfluoroalkyl, perfluoroalkoxy, methylenedioxy, ethylenedioxy, carboxyl, oxo, thioxo, imino (alkyl, aryl, aralkyl), $S(O)_n$alkyl (where n is 0-2), $S(O)_n$ aryl (where n is 0-2), $S(O)_n$ heteroaryl (where n is 0-2), $S(O)_n$ heterocyclyl (where n is 0-2), amine (mono-, di-, alkyl, cycloalkyl, aralkyl, heteroaralkyl, and combinations thereof), ester (alkyl, aralkyl, heteroaralkyl), amide (mono-, di-, alkyl, aralkyl, heteroaralkyl, and combinations thereof), sulfonamide (mono-, di-, alkyl, aralkyl, heteroaralkyl, and combinations thereof), unsubstituted aryl, unsubstituted heteroaryl, unsubstituted heterocyclyl, and unsubstituted cycloalkyl. In one aspect, the substituents on a group are independently any one single, or any subset of the aforementioned substituents.

The terms "adeninyl, cytosinyl, guaninyl, thyminyl, and uracilyl" and the like refer to radicals of adenine, cytosine, guanine, thymine, and uracil.

A "protected" moiety refers to a reactive functional group, e.g., a hydroxyl group or an amino group, or a class of molecules, e.g., sugars, having one or more functional groups, in which the reactivity of the functional group is temporarily blocked by the presence of an attached protecting group. Protecting groups useful for the monomers and methods described herein can be found, e.g., in Greene, T. W., *Protective Groups in Organic Synthesis* (John Wiley and Sons: New York), 1981, which is hereby incorporated by reference.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

The materials and methods used in the experimental examples are now described.

PBMC Isolation and Culture:

Primary human PBMC were isolated by density centrifugation using Ficoll from heparinized venous blood of HIV-1-seronegative adult donors.

p24 Assay:

HIV-1 p24 antigen was measured by commercially available ELISA kit (Zeptometrix Corp., Buffalo, N.Y.) according to manufacturer's instructions:

p27 Assay:

SIV p27 was measured by commercially available ELISA kit (Zeptometrix Corp., Buffalo, N.Y.) according to the manufacturer's instructions.

Inhibition of Type 1 Interferon Production During HIV-1 Exposure in Vitro:

Primary human PBMC were isolated by density centrifugation using Ficoll from heparinized venous blood of HIV-1-seronegative adult donors and seeded into 24-well plates at a concentration of $1 \times 10^6$ cells/mL/well. The composition being assessed (e.g., OPB-T) was diluted in propagation media (RPMI 1640 supplemented with 10% heat-inactivated FBS, 2 mM L-Glutamine, 100 U/mL penicillin and 100 µg/mL streptomycin sulfate) and subsequently added to the PBMC at a final concentration of 5 µM. Immediately following the exposure of cells to OPB-T, HIV-$1_{BaL}$ (Advanced Biotechnologies Inc., Columbia, Md.) at a final titer of $10^5$ $TCID_{50}$/mL was added to the cultures. At 24 hours post-infection, supernatants were collected by centrifugation and stored at −80° C. The quantity of IFN-α present in supernatants was determined using a commercially available ELISA system (PBL Interferon Source, Piscataway, N.J.).

The Effect of the TLR Antagonist on the Magnitude of HIV-1 Replication:

Primary human PBMC were isolated were isolated by density centrifugation using Ficoll from heparinized venous blood of HIV-1-seronegative adult donors and seeded into 24-well plates at a concentration of $1 \times 10^6$ cells/mL/well. The composition being evaluated, (e.g., OPB-T) was diluted in propagation media (RPMI 1640 supplemented with 10% heat-inactivated FBS, 2 mM L-Glutamine, 100 U/mL penicillin and 100 µg/mL streptomycin sulfate) and subsequently added to the PBMC at a final concentration of 5 µM. Immediately following the exposure of cells to the composition being evaluated, HIV-$1_{BaL}$ (Advanced Biotechnologies Inc., Columbia, Md.) at a final titer of $10^5$ $TCID_{50}$/mL was added to the cultures. In order to determine the magnitude of viral replication in the presence of the composition being evaluated, supernatants were also collected at 7 days post-infection and assayed for HIV-1 p24 antigen using an ELISA kit (Zeptometrix Corp., Buffalo, N.Y.).

Apoptosis Assay of Primary Human CD4+ and CD8+ T Lymphocytes Exposed to Type 1 Interferon:

Primary human PBMC were isolated were isolated by density centrifugation using Ficoll from heparinized venous blood of HIV-1-seronegative adult donors and seeded into 24-well plates at a concentration of $1 \times 10^6$ cells/mL/well. Freshly isolated PBMC were treated with 5 ng/mL recombinant IFN-α (PBL Interferon Source; Piscataway, N.J.) in the presence or absence of monoclonal anti-CD3 antibody (OKT3). Anti-CD3 was immobilized by coating plates with 0.1 µg/mL in PBS for 2 hours. Following a 3 day incubation period, PBMC were harvested and transferred to 24-well plates that were uncoated or coated with 5 µg/mL monoclonal anti-CD95 antibody (IgM, CH11; Immunotech, Brea, Calif.) for 14 hour at 37° C. in 5% $CO_2$. Cells were subsequently harvested, counted and stained for flow cytometry analysis. The following combinations of mAb were used to identify CD4+ and CD8+ T cell subpopulations: anti-CD3-PE/anti-CD4-APC/anti-CD8-PerCP; and for the apoptosis studies: Annexin V-Cy5.5 (eBioscience, San Diego, Calif.). One million cells were stained as previously described (Mueller Y M et al., 2001, Immunity. 15:871-882) with the combination of antibodies in HBSS (Cellgro, Herndon, Va.), 3% FBS, 0.02% $NaN_3$ for 15 min on ice, washed twice with HBSS, 3% FBS, 0.02% $NaN_3$ and fixed with 1% paraformaldehyde. Annexin V staining was performed in the presence of 2.5 mM $CaCl_2$. Analysis was performed on a FACSCalibur (Becton Dickinson, San Jose, Calif.) using FlowJo software (TreeStar, San Carlos, Calif.).

Figure 5:
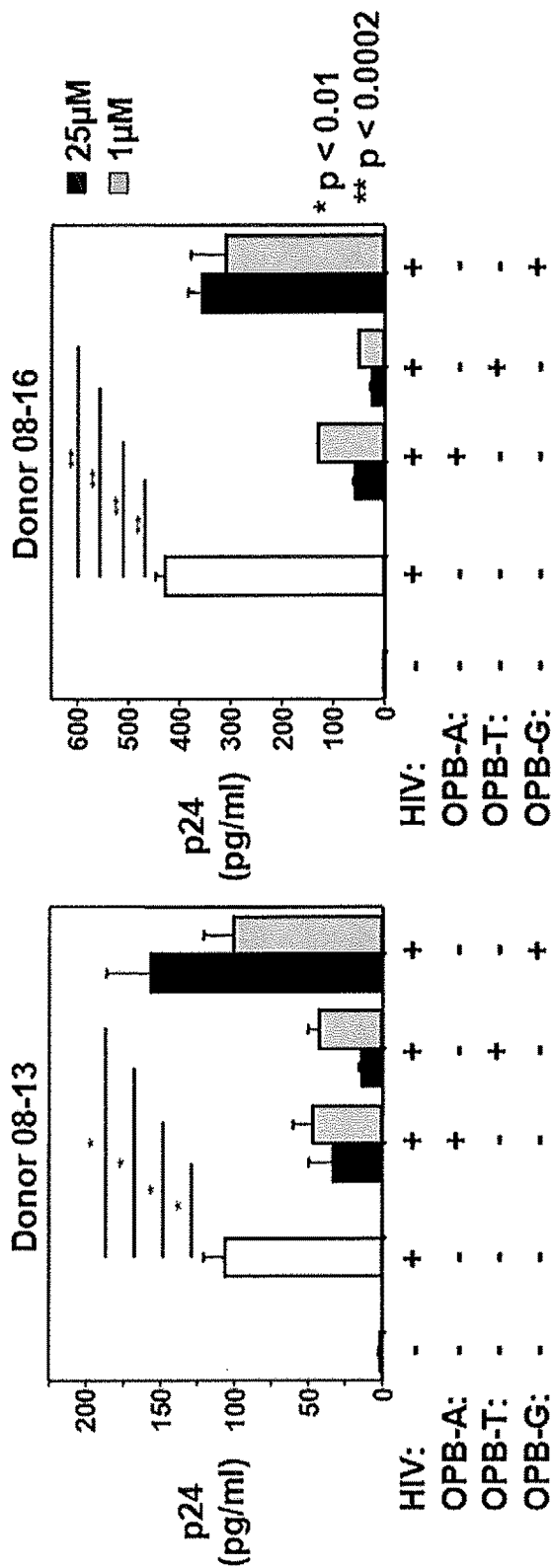
FIG. 5 depicts the results of an example experiment demonstrating that a 30-minute pre-exposure of HIV-1$_{BAL}$ virus to a nucleic acid inhibitor (here, OPB-T and OPB-A; 13-mer oligonucleotides of thymine or adenine, respectively, with phosphorothioate backbones) before human PBMC were exposed to HIV-1$_{BAL}$ ($10^5$ TCID$_{50}$/mL) inhibits infection. PBMC were activated with 10 µg/mL PHA-P and 20 U/mL IL-2 for 48 hours. Cells were then infected with 100 µl of HIV/OPB mixture for 1 hour, washed 2 times, and cultured in 1 mL fresh media. Infection was measured by HIV p24 production by ELISA 48 hours after administration of virus. Bar graph depicts mean±SE of triplicate cultures for each of 2 donors tested.

Inhibition of HIV Infection by Nucleic Acids:

PBMC isolated from healthy donors were either unstimulated (resting) or stimulated with 10 µg/mL PHA-P and 20 U/mL IL-2 (activated) for 48 hours. HIVBaL at $10^4$, $10^5$, or $10^6$ $TCID_{50}$/mL was pre-incubated with 25 µM of the composition being evaluated (e.g., OPB-T) for 30 minutes, and then cells were infected. Viral replication was measured by determining HIV p24 levels in day 2 supernatants. In such an infection inhibition assay OPB-T was effective at concentration down to 1 µM (FIG. 5). In the experiments described herein, viruses were exposed to OPB for 30 minutes before addition to cells. HIV p24 was measured by ELISA.

Inhibition of SIV Infection by Nucleic Acids:

PBMC were activated with 10 µg/mL PHA-P and 20 U/mL IL-2 for 48 hour before infection. Infections were performed with $3.7\times10^6 TCID_{50}$/mL of $SIV_{mac251}$ exposed for 30 minutes to 25 µM OPB-T before addition to PBMC. SIV viral replication was determined by measuring SIV p27 production by specific SIV p27 ELISA.

Toxicity Evaluation Using FACS Staining and Analysis:

PBMC isolated from healthy donors were either unstimulated (resting) or stimulated with 10 µg/mL PHA-P and 20 U/mL IL-2 (activated) for 48 hours. Cells were then harvested and resuspended in fresh RPMI 1840+10% FBS and treated with 25 and 100 µM OPB-T for 24 hours. Cells were harvested and stained with Annexin-V Cy5.5 and run on a FACSAria flow cytometer. Data was analyzed using FlowJo software.

Influenza Virus Infection Inhibition Animal Studies:

Specific pathogen-free 8-12 week old C57BL/6J (B6) were purchased from Jackson Laboratories. All mice are maintained in AAALAC certified barrier facilities. For intranasal (i.n.) infections the X31 (H3N2) recombinant strain of A/Aichi/2/68 and A/Puerto Rico/8/34 was used. Infections were performed intranasally with 20 µl of 30 $TCID_{50}$/ml X31 influenza virus strain in saline. Virus was preexposed to 12.3 µM for 30 minutes in PBS. At the time of infection the mice are anesthetized with Avertin (2-2-2 Tribromoethanol, 0.025 mg/g of body weight, injected intraperitoneally).

Viral Load Measurement Using Real Time PCR:

Lungs were isolated from influenza virus infected animals at different time points. Lung tissue was frozen in 1 mL of TRIzole (TRI-Reagent, Molecular Research Center, Cincinnati, Ohio) at −20° C. Tissue was homogenized, in TRIzole reagent, on ice, using a polytron blade homogenizer. RNA was extracted using the Molecular Research Center protocol followed by cleanup of the RNA with QIAGEN RNeasy Kit (Valencia, Calif.). cDNA synthesis was performed using both a specific primer (5'TCTAACCGAGGTCGAAACGTA3'; SEQ ID NO:6) and random hexamers. Real-time assays were performed in triplicate with 5 µl cDNA, 12.5 µl 2× TaqMan Universal PCR Master Mix (Applied Biosystems, Foster City, Calif.), 900 nM influenza A virus sense primer (5'-AAGACCAATCCTGTCACCTCTGA3'; SEQ ID NO:7), 900 nM influenza A virus antisense primer (5'CAAAGCGTCTACGCTGCAGTCC3'; SEQ ID NO:8), and 200 nM influenza A virus probe (FAM-5'TTTGTGTTCACGCTCACCGT3'-TAMRA; SEQ ID NO:9). All primers were specific for the influenza A virus matrix protein. Amplification and detection were performed using an ABI Prism 7900HT sequence detection system with SDS 2.2.1 software (Applied Biosystems) at the following conditions: 2 minutes at 50° C. and 10 minutes at 95° C., then 45 cycles of 15 seconds at 95° C. and 1 minute at 60° C. Viral loads were calculated as $TCID_{50}$ U/lung by comparison to an influenza viral stock standard curve run in every assay.

The results of the experiments performed are now described.

Experimental Example 1

To evaluate whether too much of a Type I interferon response during HIV infection has a deleterious effect and promotes disease by augmentation of CD95/Fas-induced apoptosis of T cells, the experiment described below was conducted. As demonstrated herein, IFN-α and IFN-β increase CD95/Fas-mediated apoptosis of CD4+ and CD8+ T cells from healthy individuals (FIG. 1). This can occur in both resting cells and cells activated through their antigen receptor (T cell receptor-TCR). It was previously shown that CD4+ T cells in HIV infection are very sensitive to CD95/Fas-mediated apoptosis (Katsikis et al., 1995, J. Exp. Med. 181:2029-2036). It was also found that HIV-specific CD8+ T cells are very susceptible to CD95/Fas-mediated apoptosis (Mueller et al., 2001, Immunity 15:871-882), which may impact viral control. The data disclosed herein suggest that IFN-α and IFN-β produced in vivo during acute and chronic HIV infection may impair the immune response against HIV and/or contribute to the loss of CD4+ T cells that is a hallmark of the disease. Type I interferons are known to inhibit cytotoxic HIV-specific CD8+ T cell responses by making these cells susceptible to CD95/Fas-mediated apoptosis.

Experimental Example 2

Figure 2:
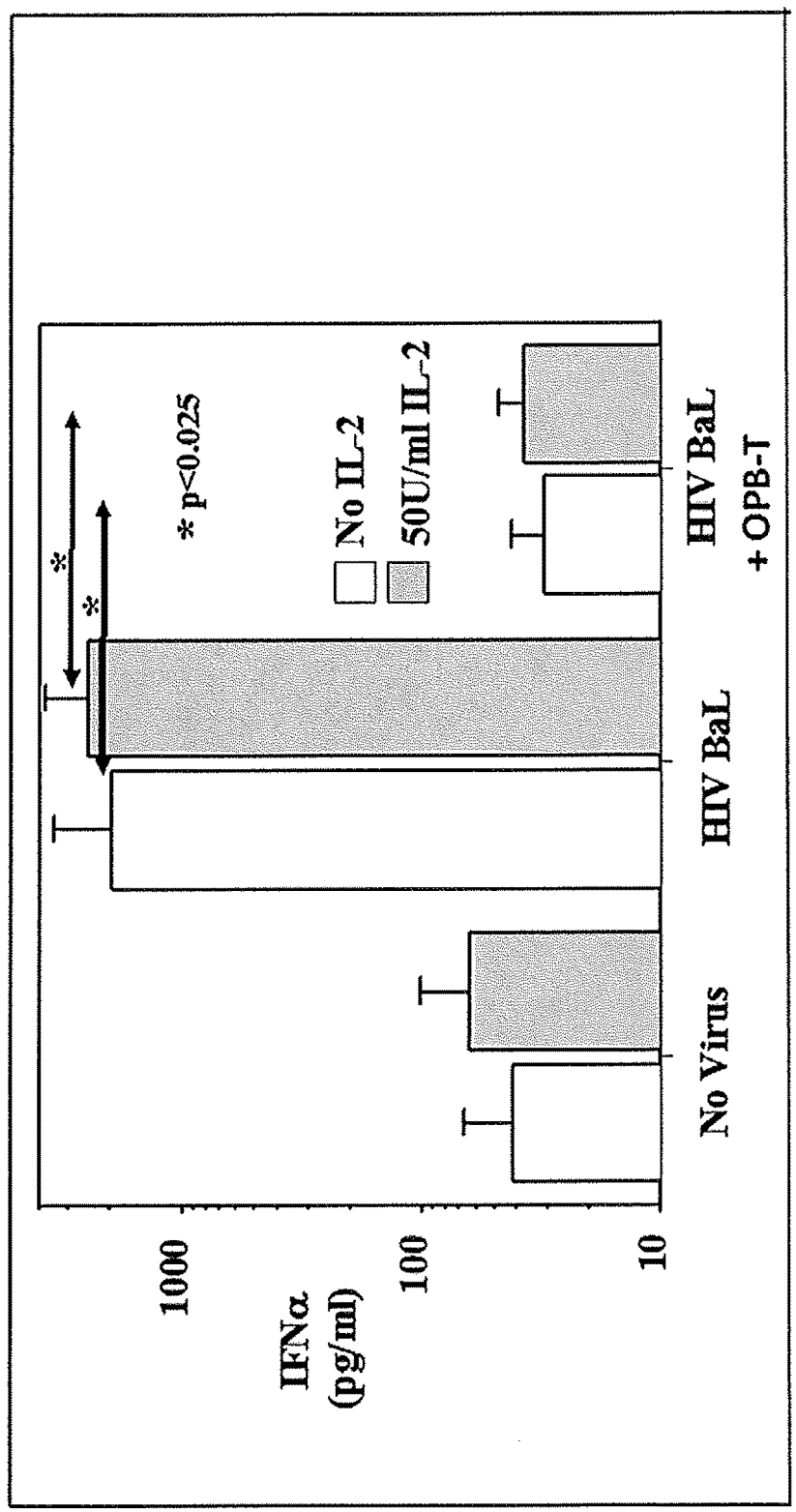
FIG. 2 depicts the results of an example experiment demonstrating that the nucleic acid inhibitor of the invention inhibits IFN-α production by PBMC exposed to HIV BaL virus. IFN-α was measured in supernatants from 24 hour cultures of PBMC from healthy donors cultured in the presence or absence of IL-2. Cultures were exposed to $10^5$ TCID$_{50}$ HIV BaL virus and treated with 5 µM OPB-T, a 13-mer oligonucleotide of thymine with a phosphorothioate backbone (n=5 for each condition).

To evaluate whether a nucleic acid inhibitor can block the production of type I interferons by HIV infection, the experiment described below was conducted. An investigation of the receptors that induce the production of Type I interferons by HIV virus has identified TLR7 as a major trigger of IFN-α and IFN-β production. Most importantly, a TLR7 inhibitor was identified that completely inhibits the production of IFN-α and IFN-β from peripheral blood mononuclear cells (PBMC) exposed to live HIV virus. The TLR7 inhibitor of the invention, administered at 5 µM, completely inhibited in vitro IFN-α production by healthy human PBMC infected by HIV virus (e.g., HIV-$1_{BaL}$ strain). PBMC exposed to $10^5$ $TCID_{50}$/mL of HIV virus for 24 hours produce 1968±1470 pg/mL of IFN-α, while TLR7 inhibitor reduces this to 31±12 pg/mL (FIG. 2, n=5 in each group). Uninfected cells produce 42±24 pg/mL (n=5). Moreover, the TLR7 inhibitor of the invention had the same effect even in the presence of IL-2, which is known to promote T cell activation and infection. Importantly, the TLR7 inhibitor of the invention had no effect on day 7 HIV p24 production (FIG. 3), a measure of viral replication in these cultures. Thus, TLR7 inhibitor inhibits Type I interferon production without affecting viral replication. Furthermore, the TLR7 inhibitor of the invention did not show any toxicity on PBMC in 24 hour assays.

Experimental Example 3

Figure 3:
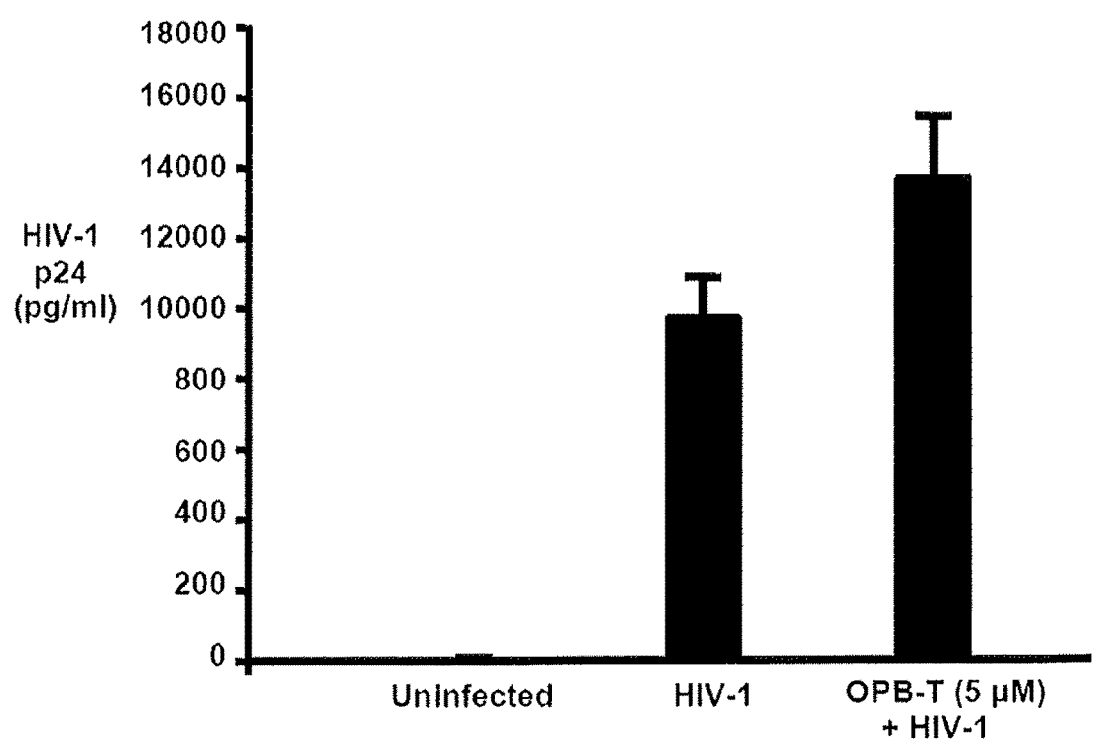
FIG. 3 depicts the results of an example experiment demonstrating that exposure of PBMC to a nucleic acid inhibitor (here, OPB-T) immediately before HIV-1$_{BAL}$ ($10^5$ TCID$_{50}$/mL) virus infection does not inhibit infection. Infection was measured by HIV p24 production by ELISA 7 days after administration of virus. n=4.
Figure 4:
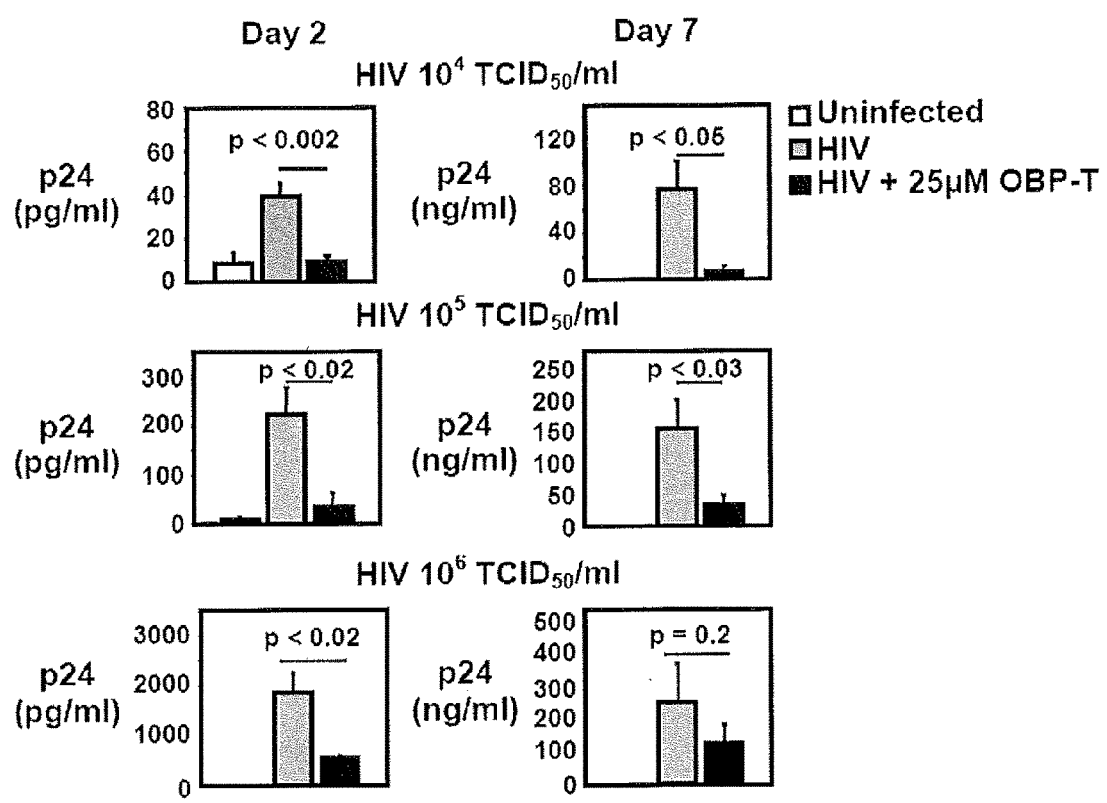
FIG. 4 depicts the results of an example experiment demonstrating that a 30-minute pre-exposure of HIV-1$_{BAL}$ virus to a nucleic acid inhibitor (here, OPB-T; a 13-mer oligonucleotide of thymine with a phosphorothioate backbone) before human PBMC were exposed to HIV-1$_{BAL}$ ($10^4$-$10^6$ TCID$_{50}$/mL) inhibits infection. PBMC from healthy human donors were activated with 10 µg/mL PHA-P and 20 U/mL IL-2 for 48 hours. Cells were then infected with 100 µl of HIV/OPB-T mixture for 1 hour, washed 2 times, and cultured in 1 mL fresh media. Infection was measured by HIV p24 production by ELISA 48 hours and 7 days after administration of virus. n=3.

The experiments described herein below are conducted to evaluate whether pre-exposure of HIV virus to a nucleic acid inhibitor could inhibit infection of PBMC with HIV virus. This assay is a more physiological assay as compared to the engineered epithelial cell line such as the P4-R5 MAGI cells that are a standard assay in microbicide development. The data disclosed herein demonstrate that a 13-mer thymine oligonucleotide (OPB-T) can interfere with the infection of human PBMC with $HIV_{BaL}$. OPB-T at 25 µM could inhibit up to $10^6$ $TCID_{50}$/mL of $HIV_{BaL}$ (FIG. 4). In human PBMC infected with $HIV_{BaL}$ pre-incubated with 25 µM OPB, HIV p24 levels in day 2 supernatants were reduced by 90.3±5.3% (p<0.002), 76±9% (p<0.02), and 63±9% (p<0.02) in cells infected with $10^4$, $10^5$, or $10^6$ TCID$_{50}$/mL HIV, respectively. In day 7 supernatants, HIV p24 levels were reduced 93±4% (p<0.05), 83±10% (p<0.03), and 59±12% (p=0.2) in cells infected with $10^4$, $10^5$, or $10^6$ TCID$_{50}$/mL HIV, respectively (FIG. 4). OPB-T was effective at concentration down to 1 µM (FIG. 5). Viruses were exposed to OPB-T for 30 minutes before by added to cells. These experiments were cell-free infections of PBMC as free virus was added to PHA activated cultures of human PBMC. Cell free infections are important because they are believed to be the predominant mode of HIV virus vaginal transmission. OPB-T is not acting on target cells to inhibit infection as addition of OPB to PBMC before exposure of cells to HIV has no inhibitory effect (FIG. 3). Although not wishing to be bound by any particular theory, the data disclosed herein are consistent with the explanation that direct contact with the virus is needed for the inhibitory effect of OPBT.

Experimental Example 4

Figure 6:
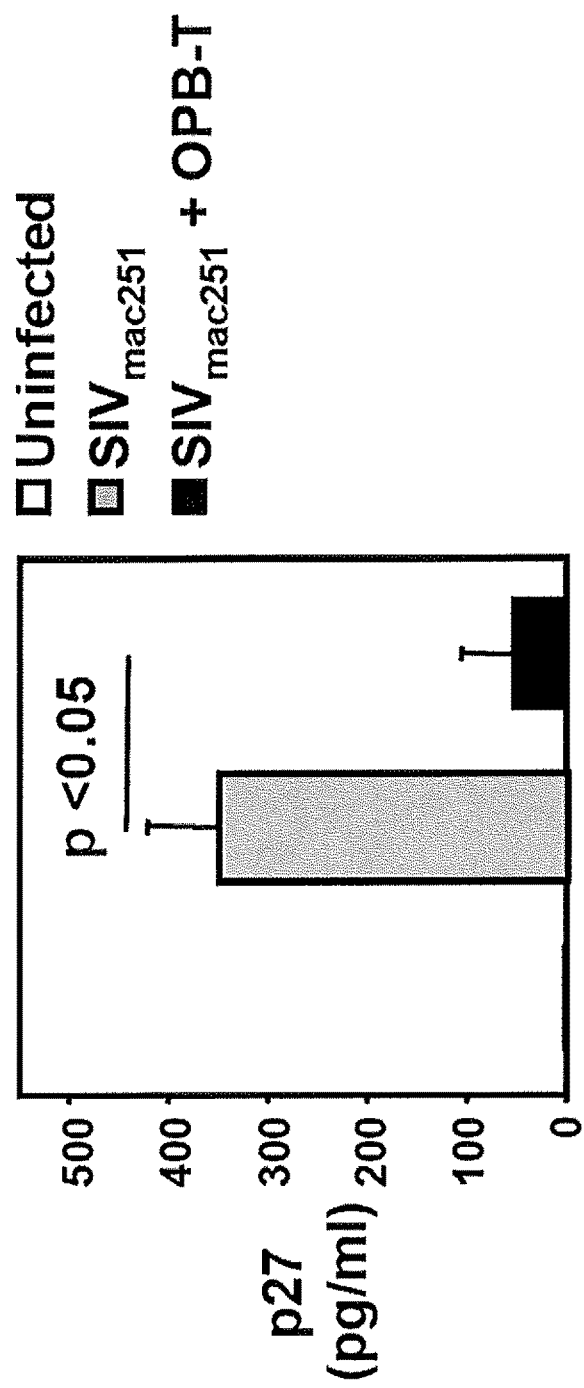
FIG. 6 depicts the results of an example experiment demonstrating that 30-minute pre-exposure of SIVmac251 virus to a nucleic acid inhibitor (here, 25 µM OPB-T; a 13-mer oligonucleotide of thymine with a phosphorothioate backbone) before rhesus macaque PBMC are exposed to SIVmac251 ($3.7\times10^6$ TCID$_{50}$/mL) inhibits infection. PBMC were activated with 10 µg/mL PHA-P and 20 U/mL IL-2 for 48 hours before infection. Infection was by SIV p27 production by ELISA 48 hours after administration of virus.
Figure 7:
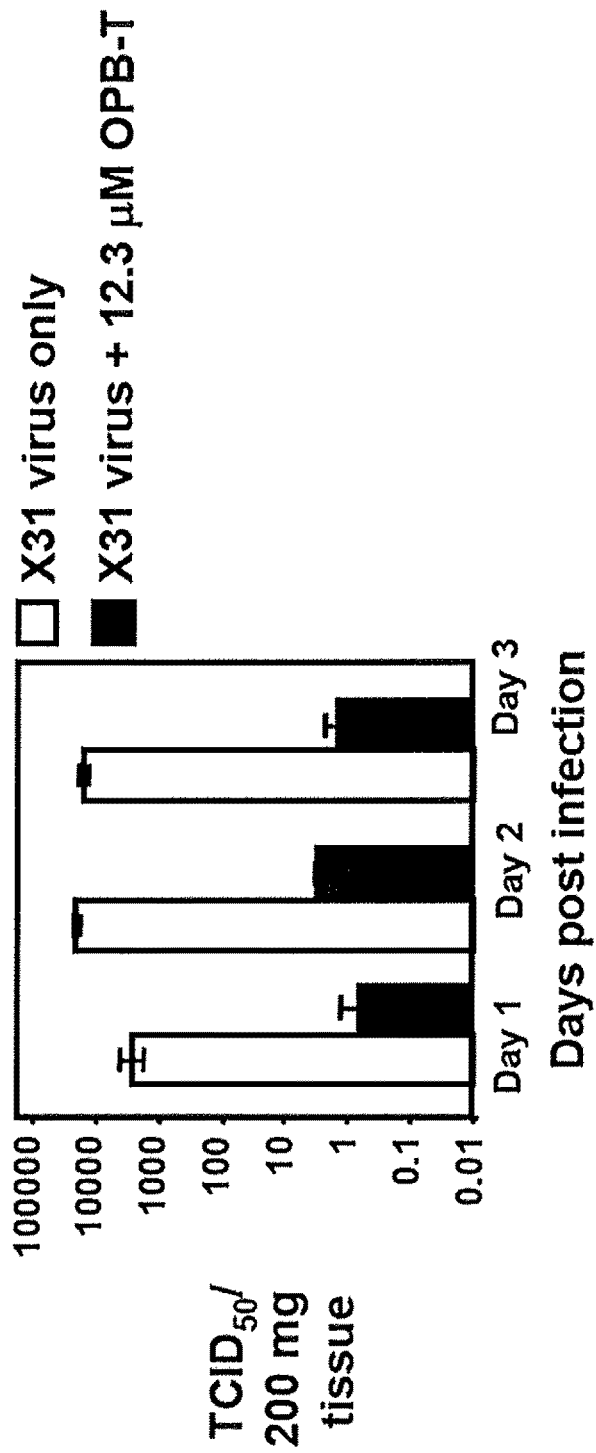
FIG. 7 depicts the results of an example experiment demonstrating that 30-minute pre-exposure of influenza type A virus (here, H3N2 strain X31) to nucleic acid inhibitor (here, 12.3 µM OPB-T; a 13-mer oligonucleotide of thymine with a phosphorothioate backbone) before intranasal application of 30 TCID$_{50}$/mL influenza virus in C57Bl/6 mice inhibited influenza virus infection in mice. Lungs of infected mice were harvested at days 1, 2 and 3 after infection and viral load was determined using real-time PCR (RT-PCR) to assess inhibition of infection. Viral load was calculated based on a standard curve derived from virus stock of known concentration. RT-PCR detection limit 0.03 TCID$_{50}$. Bars depict mean±SE, n=3 mice per time point and group.

The experiments described herein below are conducted to evaluate whether pre-exposure of SIV virus to a nucleic acid inhibitor could inhibit infection of rhesus macaque PBMC with SIV virus. As depicted in FIG. 7, OPB-T was also effective at inhibiting SIV infection/replication after cell-free infection of rhesus macaque PBMC by SIVmac251. OPB-T at 25 µM inhibited $3.7 \times 10^6$ TCID$_{50}$/mL of SIVmac251 (FIG. 6). In rhesus macaque PBMC infected with SIVmac251 pre-incubated with 25 µM OPB-T for 1 hour, SIV p27 levels in day 2 supernatants were reduced by 85% (p<0.05).

Experimental Example 5

The experiments described herein below are conducted to evaluate whether pre-exposure of influenza type A virus to a nucleic acid inhibitor inhibits infection of mice. Influenza type A virus was pre-exposed to OPB-T for 30 minutes before being applied intranasally to mice. In these experiments, OPB-T at 12.3 µM was capable of inhibiting 30 TCID$_{50}$/mL of H3N2 X31 influenza type A virus. Viral loads in the lungs of infected animals were reduced by 3-4 logs by OPB-T (FIG. 7).

Experimental Example 6

Figure 8:
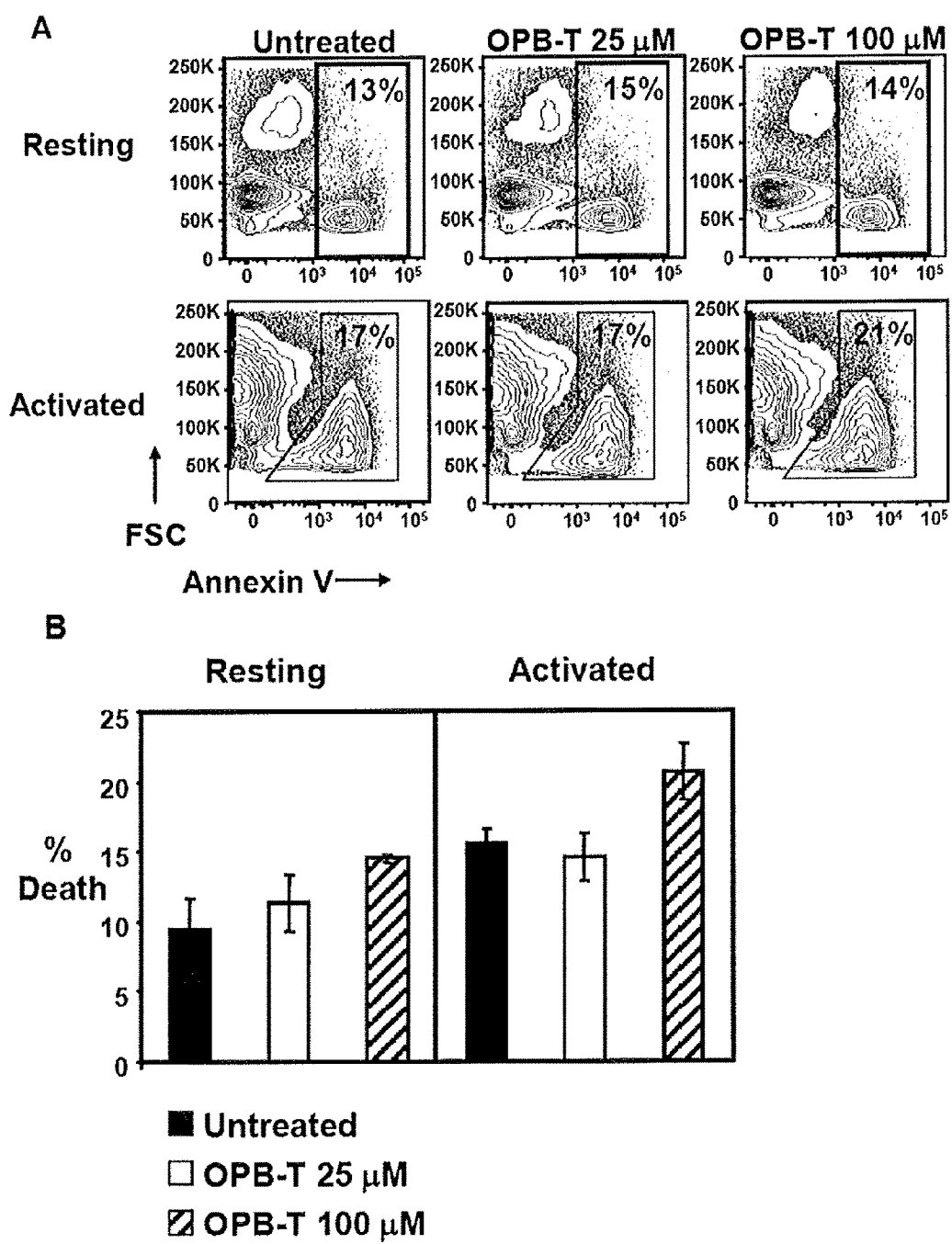
FIG. 8 depicts the results of an example experiment showing that nucleic acid inhibitor exhibits no toxicity after exposure to nucleic acid inhibitor (here, 12.3 µM OPB-T; a 13-mer oligonucleotide of thymine with a phosphorothioate backbone) for 24 hours. Toxicity was assessed by measuring cell death at 24 hours. A continuous 24-hour exposure to OPB-T had no effect on the viability of resting or activated human PBMC. PBMC's from healthy donors were either unstimulated (resting) or stimulated with 10 µg/mL PHA-P and 20 U/mL IL-2 (activated) for 48 hours. Cells were then harvested and resuspended in fresh RPMI 1840+10% FBS and treated with 25 or 100 µM OPB-T for 24 hours. Cells were harvested and stained with Annexin-V Cy5.5 and evaluated on a FACSAria flow cytometer. Data was analyzed using FlowJo software.

The evaluate the toxicity of OPB-T, freshly isolated human PBMC were incubated with OPB-T for 24 hours and then stained for cell death using annexin-V conjugated to a fluorochrome. Cells were analyzed by flow cytometry. Annexin V binds to phosphatidyl serine that is exposed on the surface of early and late apoptotic cells and necrotic cells. This very sensitive assay that can detect even small increases of cell death, OPB-T at 25 µM and 100 µM had no effect on cell viability of either resting or PHA-activated PBMC (FIGS. 8A and 8B). Unstimulated resting PBMC showed 10% cell death, while 25 µM OPB-T treated cells showed 11% cell death (FIG. 8B). In PHA-stimulated cells, 13% and 12% cell death was seen in untreated and 25 µM OPB-T treated cells, respectively (FIG. 8B). The data disclosed herein demonstrate that OPB-T has no toxicity against resting or activated human PBMC.

Experimental Example 7

To evaluate whether a nucleic acid inhibitor can block the production of type I interferons by HIV the experiment described below was conducted. An investigation of the receptors that induce the production of Type I interferons by HIV virus has identified TLR7 as a major trigger of IFN-α and IFN-β production. Most importantly, a TLR7 inhibitor was identified that completely inhibits the production of IFN-α and IFN-β from peripheral blood mononuclear cells (PBMC) exposed to live HIV virus. The TLR7 inhibitor of the invention, administered at 5 µM, completely inhibited in vitro IFN-α production by healthy human PBMC infected by HIV virus (e.g., HIV-1BaL strain). PBMC exposed to $10^5$ TCID$_{50}$/mL of HIV virus for 24 hours produce 1968±1470 pg/mL of IFN-α, while TLR7 inhibitor reduces this to 31±12 pg/mL (FIG. 2, n=5 in each group). Uninfected cells produce 42±24 pg/mL (n=5). Moreover, the TLR7 inhibitor of the invention had the same effect even in the presence of IL-2, which is known to promote T cell activation and infection. Importantly, the TLR7 inhibitor of the invention had no effect on day 7'HIV p24 production (FIG. 3), a measure of viral replication in these cultures. Thus, TLR7 inhibitor inhibits Type I interferon production without affecting viral replication. Furthermore, the TLR7 inhibitor of the invention did not show any toxicity on PBMC in 24 hour assays.

Experimental Example 8

As disclosed herein, the efficacy and safety of the baseless phosphorothioate 2' deoxyribose backbone polymer as a microbicide modulating HIV transmission was explored. The abasic 14-mer phosphorothioate 2' deoxyribose backbone (PDB) demonstrates enhanced anti-HIV-1 activity relative to homo-oligodeoxynucleotide analogs. P013 displays efficacy against both X4 and R5 HIV-1 isolates at low micromolar concentrations. PDB also exhibits an excellent in vitro safety profile in primary human cells and is chemically compatible with a universal gel-based intravaginal delivery vehicle. Most importantly, PDB possesses a dual mechanism of action against HIV-1 infection, since in addition to directly inhibiting HIV-1, it also specifically inhibits HIV induced TLR activation and cytokine production. Although not wishing to be bound by any particular theory, such HIV-induced TLR7/9-mediated immunoinflammatory response is an important aspect for the local expansion of virus from the cervigovaginal mucosa to systemic sites of infection.

Figure 9:
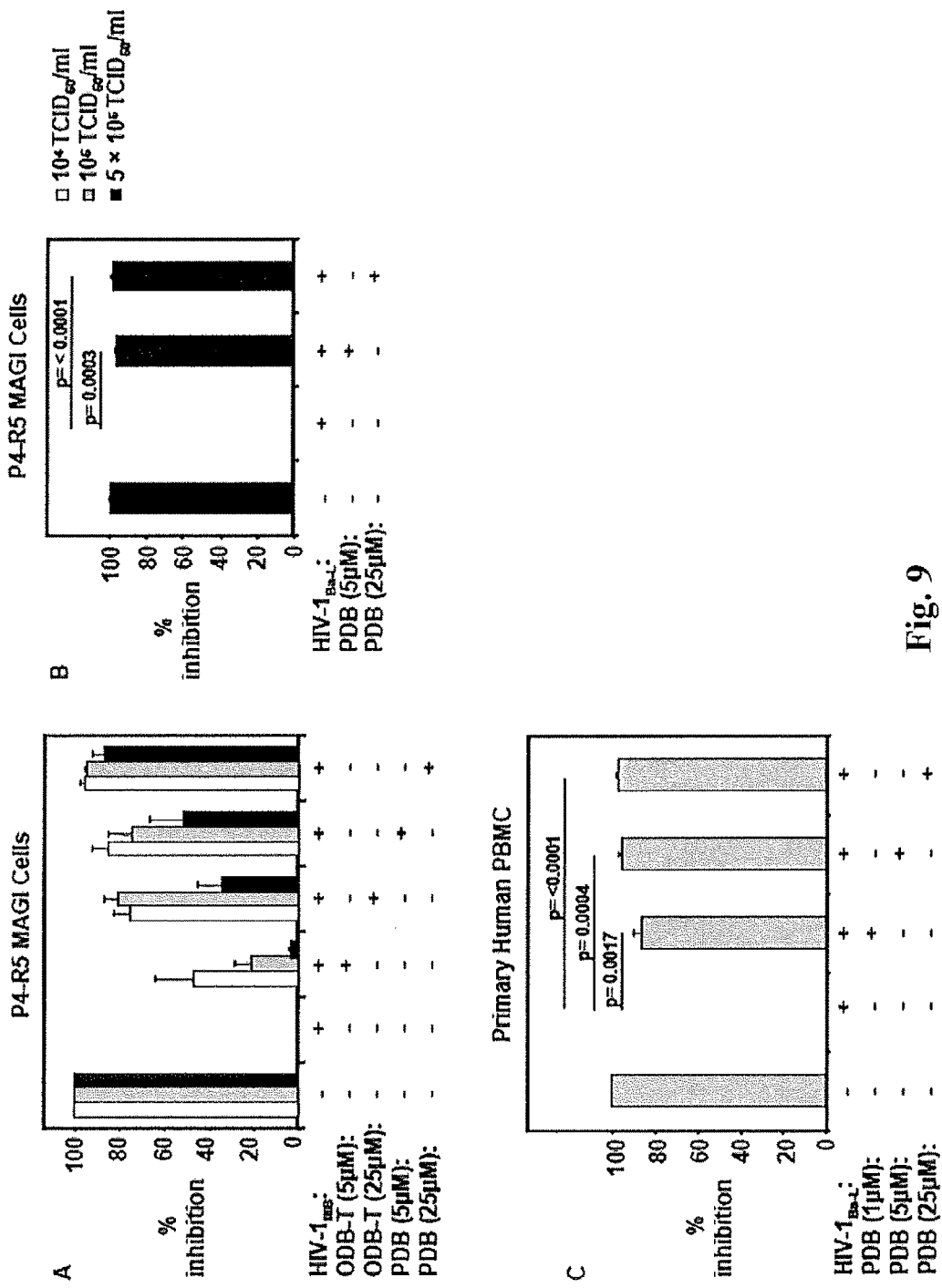
FIG. 9, comprising

PDB was assessed for its ability to inhibit cell-free HIV-1 infection of primary human PBMC and P4-R5 MAGI cells. As disclosed elsewhere herein, phosphorothioate oligonucleotide homopolymers consisting of different nucleotide bases exhibited varying degrees of anti-HIV-1 activity in primary human PBMC. At a concentration of 25 µM, PDB was approximately 2-fold more effective than 13-mer poly-T phosphorothioate 2' deoxyribose (OPB-T) at inhibiting HIV-1IIIB infection (10^4 and 10^5 TCID50/ml) in vitro (FIG. 9A). When both compounds were tested against HIV-1IIIB at a high titer of 5×10^5 TCID50/ml, 25 µM PDB inhibited infection/replication by approximately 87%±6%, while 25 µM OPB-T only reduced infectivity by 35%±10% (FIG. 9A). At titers of 10^4 and 10^5 TCID50/ml, PDB (5 µM) was more effective than OPB-T (5 µM) at reducing the magnitude of viral infection/replication by approximately ~2-fold and 3-fold, respectively (FIG. 9A). PDB at concentrations of 5 µM and 25 µM also significantly inhibited HIV-1BaL (5×10^5 TCID50/ml) infection of P4-R5 MAGI by 96%±2% and 99%±0.5%, respectively (FIG. 9B). When tested against infection of primary cells, at a low concentration of 1 µM, PDB inhibited HIV-1BaL infection of primary human PBMC by 87%±4% (FIG. 9C). At concentrations of 5 µM and 25 µM PDB completely inhibited HIV-1BaL infection of PBMC (FIG. 9C). PDB is very effective at inhibiting HIV-1 infection.

Figure 10:
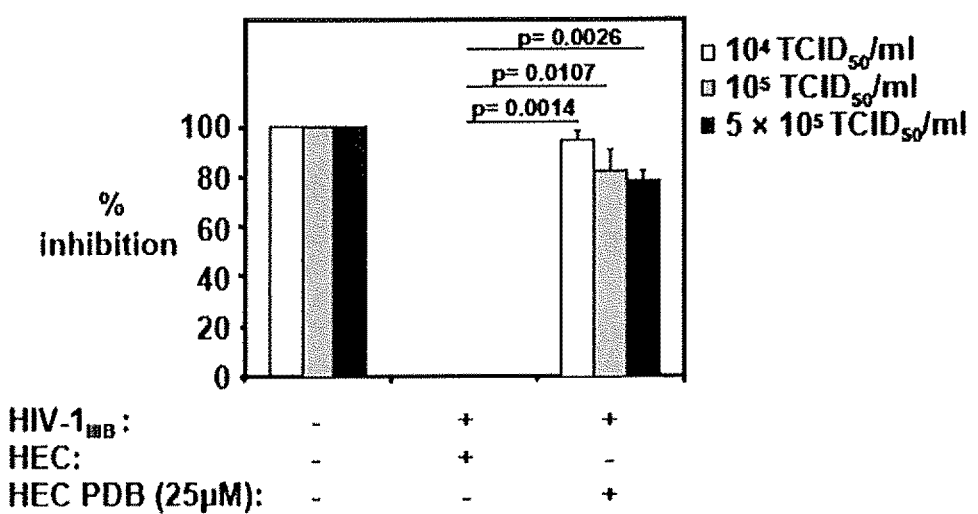
FIG. 10 depicts the results of an example experiment demonstrating that a PDB HydroxyEthyl Cellulose (HEC) gel formulation can inhibit cell-free HIV$_{IIIB}$ infection of P4-R5 MAGI cells. PDB HEC gel formulation (25 µM; pH 4.4) inhibited β-gal expression by P4-R5 MAGI cells infected with 10^4, 10^5 and 5×10^5 TCID50/ml TCID50/ml of HIV-1IIIB. HIV-1 was exposed for 30 minutes to 25 µM of formulated PDB before the HIV/PDB gel mixture was added to P4-R5 MAGI cells. β-gal expression was measured 48 hours later (n=3).

A PDB hydroxyethylcellulose (HEC) gel formulation was assessed for its ability to inhibit cell-free HIV-1 infection of P4-R5 MAGI cells. Formulation of a microbicide into a gel is useful for a topical application, as this allows for a more uniform intravaginal dispersion and increases retainment at the application site. For the example experiments described herein, HEC gel was selected as a vehicle for vaginal delivery and retainment of the assessed phosphorothioate inhibitors. HEC gel has been studied extensively and does not induce toxicity or inflammation in the vaginal mucosa (Tien et al, 2005, AIDS Res Hum Retroviruses 21:845-853). In order to assess whether PDB microbicide gel is likely to be active in vivo, the pH of the formulation was initially adjusted to the pH of the vaginal environment (pH 4.4). Furthermore, the addition of media to the virus/gel mixture following a preincubation period at physiologic temperature mimics the pH change/transition that occurs when semen is introduced into the vaginal canal. In the presence of gel and pH transition, PDB at a concentration of 25 µM reduced the infectivity of cell-free HIV-1IIIB at titers of $10^4$ TCID50/ml and $5\times10^5$ TCID^50/ml by approximately 100%±4% and 77%±2%, respectively. (FIG. 10).

Figure 11:
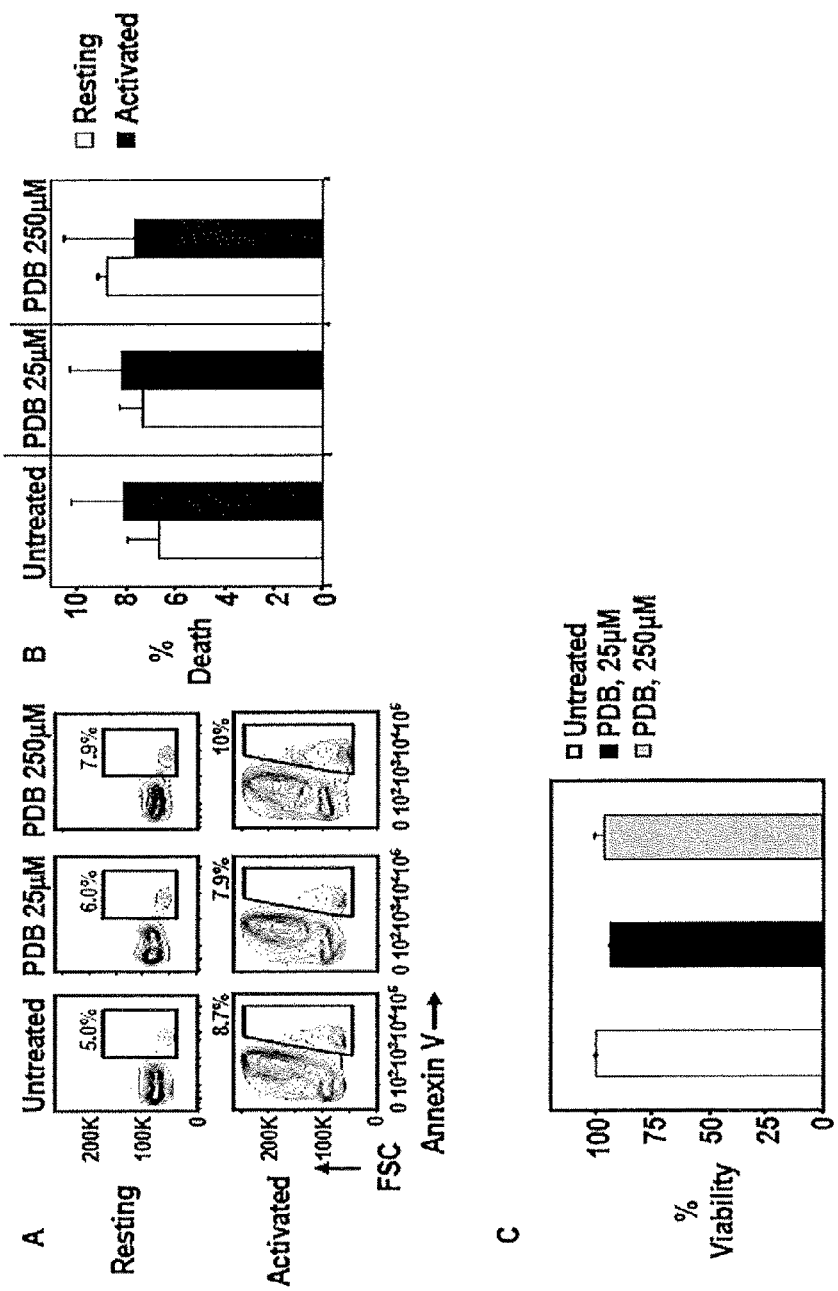
FIG. 11, comprising

PDB exhibits no toxicity on primary human PBMC and does not affect the viability of human uterine epithelial HEC-1-A cells. To further exclude possible toxicity associated with PDB, it was tested against human peripheral blood mononuclear cells and the human uterine epithelial HEC-1-A cell line. To assess, freshly isolated human PBMC were incubated with PDB for 24 hours (continuous exposure) and subsequently stained for cell death using annexin-V conjugated to a fluorochrome. Cells were analyzed by flow cytometry. Annexin V binds to phosphatidyl serine that is exposed on the surface of early and late apoptotic cells and necrotic cells. In this very sensitive assay that can detect even small increases in cell death, PDB at 25 µM and 250 µM concentrations did not induce any cell death (FIGS. 11A and 11B). The effect of PDB on HEC-1-A cells FIG. 11C shows the viability of HEC-1-A cells after 24 hours of continuous exposure to PDB at a concentration of 250 µM, which is approximately ten times higher than the effective anti-viral concentration and fifty times greater than the optimal immunomodulatory dose. Even at this high concentration and after continuous exposure to PDB, epithelial cell viability was not reduced (FIG. 11C).

Figure 12:
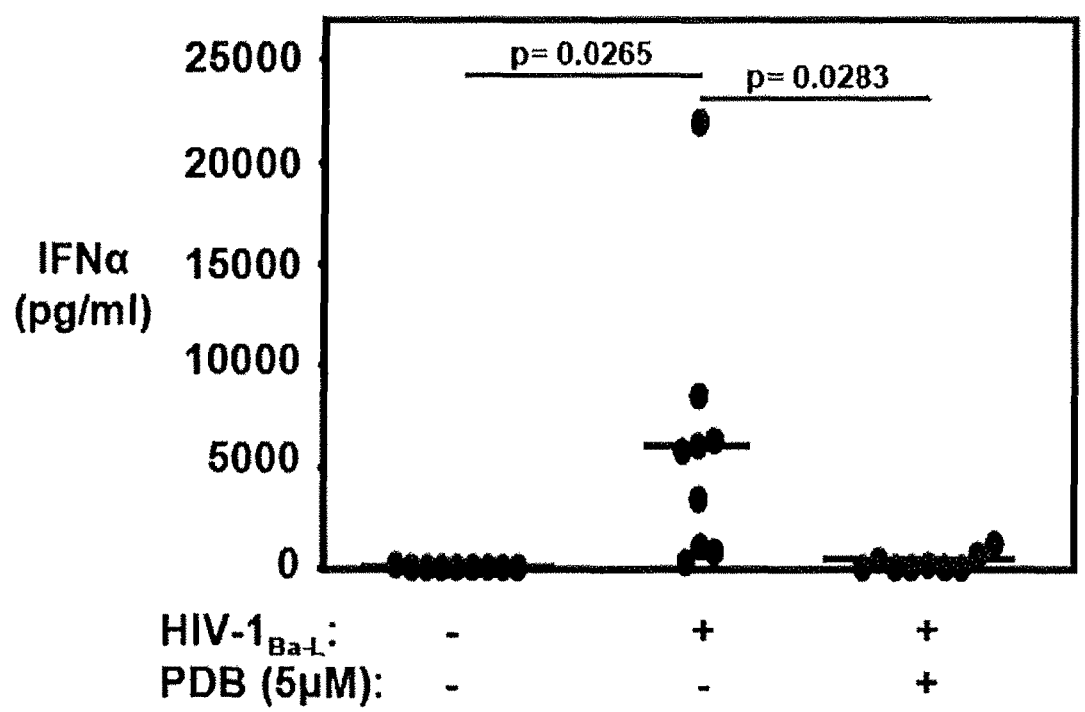
FIG. 12 depicts the results of an example experiment demonstrating that PDB inhibits HIV-1-induced IFN-α production from primary human PBMC. PDB inhibits the generation of IFN-α from primary human PBMC and this effect is independent of DNA immunoregulatory sequence specificity. Following isolation, cells were resuspended in fresh RPMI 1640 with 10% FBS, treated with 5 µM PDB and immediately infected with HIV-1$_{BaL}$. At 24 hours post-infection, IFN-α were measured in cell-free supernatants by ELISA (n=7).

PDB inhibits HIV-1-induced IFNα production from primary human PBMC. Abasic phosphorothioate deoxyribose backbones have been reported to be TLR7/TLR9-specific antagonists. HIV-1-induced IFNα production by pDC results from TLR7 and TLR9 signaling triggered by HIV-1 recognition, HIV-1-induced IFNα production by pDC results from TLR7 and TLR9 signaling triggered by HIV-1 recognition (Beignon et al., 2005, J Clin Invest 115:3265-3275; Meier et al., 2007, J Viral 81:8180-8191). Since the elicitation of a type 1 interferon response at the portal of viral entry may drive local expansion and dissemination to peripheral sites of infection (Li et al., 2009, Nature 458:1034-1038; Wang et al., 2005, J Virol 79:14355-14370), it was assessed whether PDB could suppress IFNα production during HIV-1 infection of PBMC in vitro. At low concentrations, PDB markedly reduced the generation of IFNα from PBMC exposed to HIV-1 (FIG. 12). This antagonistic effect did not require cells to be pre-incubated with the compound prior to infection.

OTHER EMBODIMENTS

While the invention has been disclosed with reference to specific embodiments, it is apparent that other embodiments and variations of the invention may be devised by others skilled in the art without departing from the true spirit and scope of the invention. The appended claims are intended to be construed to include all such embodiments and equivalent variations.

The disclosures of each and every patent, patent application, and publication cited herein are hereby incorporated herein by reference in their entirety.

The invention claimed is:

1. A pharmaceutical composition comprising a nearly baseless backbone nucleic acid inhibitor;
   wherein the inhibitor is about 10 nucleotides to about 30 nucleotides long; and
   wherein the nucleotide at the 3'- or 5'-end of the inhibitor comprises a nucleic acid base and the remaining nucleotides in the inhibitor are abasic.

2. The composition of claim 1, wherein the inhibitor comprises a backbone selected from the group consisting of a DNA backbone, a RNA backbone, and any combinations thereof.

3. The composition of claim 1, wherein the backbone of the inhibitor comprises at least one linkage selected from the group consisting of phosphorothioate, phosphoroselenate, boranophosphate, borano phosphate ester, hydrogen phosphonate, alkyl or aryl phosphonate, phosphotriester, methylenephosphonate, sulfone, sulfate, ketyl, phosphorodithioate, phosphoroamidate and phosphate ester.

4. The composition of claim 1, wherein the inhibitor is selected from the group consisting of single-stranded and double-stranded.

5. The composition of claim 1, wherein the inhibitor is selected from the group consisting of from about 10 to about 15 nucleotides long, from about 15 to about 20 nucleotides long, from about 20 to about 25 nucleotides long, and from about 25 to about 30 nucleotides long.

6. The composition of claim 1, wherein at least one nucleotide in the inhibitor comprises a modification selected from the group consisting of 2-O'-methyl, 2'-fluorine, 2'-O-methoxyethyl, 2'-O-aminopropyl, 2'-amino, locked nucleotide (LNA) and 2',4'-ethylene bridged nucleotide.

* * * * *

SEQUENCE LISTING

```
<160> NUMBER OF SEQ ID NOS: 9

<210> SEQ ID NO 1
<211> LENGTH: 30
<212> TYPE: DNA
<213> ORGANISM: Artificial Sequence
<220> FEATURE:
<223> OTHER INFORMATION: chemically synthesized

<400> SEQUENCE: 1
tttttttttt tttttttttt tttttttttt                                    30

<210> SEQ ID NO 2
<211> LENGTH: 30
<212> TYPE: DNA
<213> ORGANISM: Artificial Sequence
<220> FEATURE:
<223> OTHER INFORMATION: chemically synthesized

<400> SEQUENCE: 2
aaaaaaaaaa aaaaaaaaaa aaaaaaaaaa                                    30

<210> SEQ ID NO 3
<211> LENGTH: 30
<212> TYPE: DNA
<213> ORGANISM: Artificial Sequence
```

```
<220> FEATURE:
<223> OTHER INFORMATION: chemically synthesized

<400> SEQUENCE: 3
gggggggggg gggggggggg gggggggggg                              30

<210> SEQ ID NO 4
<211> LENGTH: 30
<212> TYPE: DNA
<213> ORGANISM: Artificial Sequence
<220> FEATURE:
<223> OTHER INFORMATION: chemically synthesized

<400> SEQUENCE: 4
cccccccccc cccccccccc cccccccccc                              30

<210> SEQ ID NO 5
<211> LENGTH: 30
<212> TYPE: DNA
<213> ORGANISM: Artificial Sequence
<220> FEATURE:
<223> OTHER INFORMATION: chemically synthesized

<400> SEQUENCE: 5
uuuuuuuuuu uuuuuuuuuu uuuuuuuuuu                              30

<210> SEQ ID NO 6
<211> LENGTH: 21
<212> TYPE: DNA
<213> ORGANISM: Influenza A virus

<400> SEQUENCE: 6
tctaaccgag gtcgaaacgt a                                       21

<210> SEQ ID NO 7
<211> LENGTH: 23
<212> TYPE: DNA
<213> ORGANISM: Influenza A virus

<400> SEQUENCE: 7
aagaccaatc ctgtcacctc tga                                     23

<210> SEQ ID NO 8
<211> LENGTH: 22
<212> TYPE: DNA
<213> ORGANISM: Influenza A virus

<400> SEQUENCE: 8
caaagcgtct acgctgcagt cc                                      22

<210> SEQ ID NO 9
<211> LENGTH: 20
<212> TYPE: DNA
<213> ORGANISM: Influenza A virus

<400> SEQUENCE: 9
tttgtgttca cgctcaccgt                                         20
```